(12) United States Patent
Shouldice et al.

(10) Patent No.: US 12,207,904 B2
(45) Date of Patent: Jan. 28, 2025

(54) APPARATUS, SYSTEM, AND METHOD FOR PHYSIOLOGICAL SENSING IN VEHICLES

(71) Applicant: ResMed Sensor Technologies Limited, Sandyford (IE)

(72) Inventors: Redmond Shouldice, Sandyford (IE); Stephen Mcmahon, Sandyford (IE)

(73) Assignee: ResMed Sensor Technologies Limited (IE)

( * ) Notice: Subject to any disclaimer, the term of this patent is extended or adjusted under 35 U.S.C. 154(b) by 0 days.

(21) Appl. No.: 18/333,035

(22) Filed: Jun. 12, 2023

(65) Prior Publication Data
US 2024/0023816 A1 Jan. 25, 2024

Related U.S. Application Data

(63) Continuation of application No. 15/733,174, filed as application No. PCT/EP2018/086765 on Dec. 21, 2018, now Pat. No. 11,707,197.
(Continued)

(51) Int. Cl.
*A61B 5/0205* (2006.01)
*A61B 5/08* (2006.01)
(Continued)

(52) U.S. Cl.
CPC .......... *A61B 5/0205* (2013.01); *A61B 5/0816* (2013.01); *A61B 5/113* (2013.01);
(Continued)

(58) Field of Classification Search
CPC ..... A61B 5/0205; A61B 5/0816; A61B 5/113; A61B 2562/0219; A61B 5/163;
(Continued)

(56) References Cited

U.S. PATENT DOCUMENTS 6,661,345 B1 12/2003 Bevan et al.
RE42,471 E 6/2011 Torch
(Continued)

FOREIGN PATENT DOCUMENTS

CN 101917903 A 12/2010
CN 204306833 U 5/2015
(Continued)

OTHER PUBLICATIONS

Office Action issued in corresponding Japanese Patent Application No. 2020-534935, mailed Sep. 1, 2023, 10 pages.
(Continued)

*Primary Examiner* — Omeed Alizada
(74) *Attorney, Agent, or Firm* — Botos Churchill IP Law LLP

(57) ABSTRACT

Methods and apparatus provide physiological movement detection, such as gesture, breathing, cardiac and/or gross motion, such as with sound, radio frequency and/or infrared generation, by electronic devices such as vehicular processing devices. The electronic device in a vehicle may, for example, be any of an audio entertainment system, a vehicle navigation system, and a semi-autonomous or autonomous vehicle operations control system. One or more processors of the device, may detect physiological movement by controlling producing sensing signal(s) in a cabin of a vehicle housing the electronic device. The processor(s) control sensing, with a sensor, reflected signal(s) from the cabin. The processor(s) derive a physiological movement signal with the sensing signal and reflected signal and generate an output based on an evaluation of the derived physiological movement signal. The output may control operations or provide an input to any of the entertainment system, navigation system, and vehicle operations control system.

20 Claims, 12 Drawing Sheets

Related U.S. Application Data

(60) Provisional application No. 62/609,998, filed on Dec. 22, 2017.

(51) Int. Cl.
*A61B 5/113* (2006.01)
*A61M 21/02* (2006.01)

(52) U.S. Cl.
CPC ...... *A61B 2562/0219* (2013.01); *A61M 21/02* (2013.01); *A61M 2205/3375* (2013.01); *A61M 2230/63* (2013.01)

(58) Field of Classification Search
CPC ....... A61B 2503/22; A61B 5/18; A61B 5/117; A61B 5/02416; A61B 5/05; A61B 5/1102; A61B 5/6893; A61B 5/7267; A61B 5/4809; A61M 21/02; A61M 2205/3375; A61M 2230/63; A61M 2021/0027; A61M 2021/0083; B60W 40/00; B60W 50/14; B60W 40/08; B60W 2040/0872; B60W 60/001; B60W 60/0053; B60W 2040/0827; B60W 2040/0881; B60W 2050/0005; B60W 2050/0052; B60W 2050/0057; B60W 2420/40; B60W 2420/54; B60W 2540/18; B60W 2556/50; G01C 21/3407; B60H 1/00821; G05D 1/0061; G05D 1/0088; G05D 2201/0213

See application file for complete search history.

(56) References Cited

U.S. PATENT DOCUMENTS

| | | | |
|---|---|---|---|
| 8,562,526 | B2 | 10/2013 | Heneghan et al. |
| 8,841,994 | B2 | 9/2014 | Li |
| 8,874,301 | B1 | 10/2014 | Rao et al. |
| 9,430,938 | B2 | 8/2016 | Proud |
| 9,489,817 | B2 | 11/2016 | Gui |
| 9,500,489 | B1 | 11/2016 | Ng |
| 9,862,271 | B2 | 1/2018 | Brankovic et al. |
| 9,883,821 | B2 | 2/2018 | Muehlsteff |
| 9,993,166 | B1 | 6/2018 | Johnson et al. |
| 10,004,451 | B1 | 6/2018 | Proud |
| 10,004,873 | B1 * | 6/2018 | Hur .......... A61B 5/48 |
| 10,009,581 | B2 | 6/2018 | Proud |
| 10,159,421 | B2 | 12/2018 | Heneghan |
| 2004/0039254 | A1 | 2/2004 | Stivoric et al. |
| 2005/0073424 | A1 * | 4/2005 | Ruoss .......... A61B 5/18 342/61 |
| 2008/0077015 | A1 | 3/2008 | Boric-Lubecke et al. |
| 2008/0183388 | A1 | 7/2008 | Goodrich |
| 2010/0240945 | A1 | 9/2010 | Bikko |
| 2011/0068935 | A1 | 3/2011 | Riley et al. |
| 2012/0150387 | A1 | 6/2012 | Watson et al. |
| 2013/0172770 | A1 * | 7/2013 | Muehlsteff .......... A61B 5/486 600/534 |
| 2013/0231579 | A1 | 9/2013 | Shigeto |
| 2013/0345921 | A1 | 12/2013 | Al-Ali et al. |
| 2014/0163343 | A1 | 6/2014 | Heneghan et al. |
| 2014/0276165 | A1 | 9/2014 | Addison et al. |
| 2014/0277822 | A1 * | 9/2014 | Nunn .......... A47C 27/083 700/301 |
| 2015/0193193 | A1 | 7/2015 | Khaira et al. |
| 2015/0223731 | A1 | 8/2015 | Sahin |
| 2015/0325270 | A1 | 11/2015 | Utsunomiya et al. |
| 2016/0357185 | A1 | 12/2016 | Laur et al. |
| 2017/0143253 | A1 | 5/2017 | Krenzer et al. |
| 2017/0180911 | A1 | 6/2017 | Burton |
| 2017/0212235 | A1 | 7/2017 | Qiu et al. |
| 2017/0232915 | A1 | 8/2017 | Dufford |
| 2017/0341658 | A1 | 11/2017 | Fung et al. |
| 2017/0347951 | A1 | 12/2017 | Gollakota et al. |
| 2018/0022358 | A1 | 1/2018 | Fung et al. |
| 2018/0203451 | A1 | 7/2018 | Cronin et al. |
| 2018/0287651 | A1 | 10/2018 | Fernando et al. |
| 2018/0290020 | A1 | 10/2018 | Vissa et al. |
| 2019/0133511 | A1 * | 5/2019 | Migneco .......... A61B 5/4064 |
| 2020/0365275 | A1 | 11/2020 | Barnett et al. |
| 2021/0150873 | A1 | 5/2021 | Shouldice et al. |
| 2023/0248935 | A1 | 8/2023 | Shouldice et al. |

FOREIGN PATENT DOCUMENTS

| | | | |
|---|---|---|---|
| CN | 106456000 | A | 2/2017 |
| DE | 10259522 | A1 | 7/2004 |
| DE | 102008038022 | A1 | 3/2009 |
| DE | 102015122245 | A1 | 6/2017 |
| EP | 1308812 | A2 | 5/2003 |
| EP | 2637385 | A2 | 9/2013 |
| EP | 2638855 | A1 | 9/2013 |
| FR | 3028741 | A1 | 5/2016 |
| JP | 2005537721 | A | 12/2005 |
| JP | 2006510880 | A | 3/2006 |
| JP | 2010012018 | A | 1/2010 |
| JP | 2012239748 | A | 12/2012 |
| JP | 2014138661 | A | 7/2014 |
| JP | 2016107095 | A | 6/2016 |
| JP | 2016532481 | A | 10/2016 |
| JP | 2016193020 | A | 11/2016 |
| JP | 2017064338 | A | 4/2017 |
| KR | 20150072821 | A | 6/2015 |
| KR | 20170015214 | A | 2/2017 |
| WO | 2004021134 | A2 | 3/2004 |
| WO | 2004100100 | A1 | 11/2004 |
| WO | 2008057883 | A2 | 5/2008 |
| WO | 2007143535 | A3 | 8/2008 |
| WO | 2010036700 | A1 | 4/2010 |
| WO | 2010091168 | A1 | 8/2010 |
| WO | 2013177621 | A1 | 12/2013 |
| WO | 2014015238 | A1 | 1/2014 |
| WO | 2014047310 | A1 | 3/2014 |
| WO | 2015006364 | A2 | 1/2015 |
| WO | 2015041892 | A1 | 3/2015 |
| WO | 2015054134 | A1 | 4/2015 |
| WO | 2015061848 | A1 | 5/2015 |
| WO | 2015179911 | A1 | 12/2015 |
| WO | 2016021235 | A1 | 2/2016 |
| WO | 2016093927 | A2 | 6/2016 |
| WO | 2016145483 | A1 | 9/2016 |
| WO | 2016170005 | A1 | 10/2016 |
| WO | 2016170011 | A1 | 10/2016 |
| WO | 2016188826 | A1 | 12/2016 |
| WO | 2017024085 | A1 | 2/2017 |
| WO | 2017029284 | A1 | 2/2017 |
| WO | 2017029317 | A1 | 2/2017 |
| WO | 2017032873 | A2 | 3/2017 |
| WO | 2017032873 | A3 | 4/2017 |
| WO | 2017097907 | A1 | 6/2017 |
| WO | 2017098609 | A1 | 6/2017 |
| WO | 2017100605 | A1 | 6/2017 |
| WO | 2017102614 | A1 | 6/2017 |

OTHER PUBLICATIONS

Examination Report issued in corresponding EP application No. 18833058.3 on Jan. 4, 2022.
Examination Report issued in corresponding EP application No. 18833244.9 on Jan. 3, 2022.
Final OA mailed Mar. 8, 2022 for U.S. Appl. No. 15/733,162.
First Office Action issued in corresponding Chinese Patent Application No. 201880087490.X, mailed Dec. 5, 2022, 30 pages.
Non Final Office Action mailed Sep. 21, 2021 for U.S. Appl. No. 15/733,162.
Notice of Allowance issued in Japanese Patent Application No. 2020-534829, mailed Nov. 25, 2022, 3 pages.
Office Action for corresponding EP Application No. 18833058.3-1113 dated Jul. 15, 2022.
Office Action for corresponding European Patent Application No. 18833244.9-1126, dated Jul. 1, 2022.

(56) References Cited

OTHER PUBLICATIONS

Office Action from corresponding CN Application No. 201880087497.1 dated Jan. 18, 2023, 11 pages.
Office Action issued in corresponding Japanese Patent Application No. 2020-534898, mailed Nov. 22, 2022, 12 pages.
Office Action issued in corresponding Japanese Patent Application No. 2020-534935, mailed Nov. 22, 2022, 17 pages.
Office Action issued in corresponding Korean Patent Application No. 10-2020-7021037, mailed Feb. 28, 2023, 22 pages.
Partial International Search Report issued on Mar. 25, 2019.
PCT International Search Report issued in corresponding PCT application No. PCT/EP2018/086764 on May 29, 2019.
Restriction Requirement Office Action dated Jun. 14, 2021 for U.S. Appl. No. 15/733,162.
"Sleep as Android", https://sleep.urbandroid.org/https://sleep.urbandroid.org/documentation/.
"SleepScore", https://www.medgadget.com/2017/11/sleepscore-labs-releases-contact-free-sleep-monitoring-system.html https://www.sleepscore.com/sleepscore-high-low/, Nov. 15, 2017.
Condliffe, Jamie , "This App Lets You Control Your Phone Using Sonar", https://www.technologyreview.com/s/602834/this-app-lets-you-control-your-phone-using-sonar/, Nov. 15, 2016.
Nandakumar, Rajalakshmi , et al., "Contactless Sleep Apnea Detection on Smartphones", May 18, 2015.
Sangeetha, M. , et al., "Embedded ECG Based Real Time Monitoring and Control of Driver Drowsiness Condition", http://article.sciencepublishinggroup.com/html/10.11648.j.ijsts.20150304.17.html, Jul. 2015.
Shin, Heung-Sub , "Real Time Car Driver's Condition Monitoring System", http://web.ee.nchu.edu.tw/~ljh/paper/Real Time Car Driver's Condition Monitoring System.pdf, Jul. 2010.
Wang, Xuyu , et al., "SonarBeat: Sonar Phase for Breathing Beat Monitoring with Smartphones", Department of Electrical and Computer Engineering, Auburn University, Auburn, AL 36849-5201, USA, Aug. 3, 2017.
Office Action issued in corresponding Korean Patent Application No. 10-2020-7021041, mailed Feb. 16, 2024, 19 pages.

\* cited by examiner

APPARATUS, SYSTEM, AND METHOD FOR PHYSIOLOGICAL SENSING IN VEHICLES

1 CROSS REFERENCE TO RELATED APPLICATIONS

This application is a continuation of U.S. patent application Ser. No. 15/733,174, filed on Jun. 4, 2020, which is a national phase entry under 35 U.S.C. § 371 of International Application No. PCT/EP2018/086765 filed Dec. 21, 2018, published in English which claims priority from U.S. Provisional Patent Application No. 62/609,998, filed Dec. 22, 2017, the entire contents of each are incorporated herein by reference.

2 BACKGROUND OF THE TECHNOLOGY

2.1 Field of the Technology

The present technology relates to detecting bio-motion associated with living subjects with in-vehicle equipment. More particularly, the present technology relates to sensing systems for vehicles to detect physiological characteristics such as physiological movement such as breathing movement and cardiac movement and/or to detect other less cyclical body movement of a living subject.

2.2 Description of the Related Art

Monitoring the breathing and body (including limb) movement of a person, for example, prior to or during sleep, can be useful in many ways. For example, such monitoring could be useful in detecting sleepiness. Traditionally, the barrier to entry for active radio location or ranging implementations is that specialized hardware circuitry and antennas are required.

Smartphones and other portable and inconspicuous processing or electronic communication devices have been ubiquitous in daily life, even in developing countries where landlines are not available. For example, many vehicles contain audio devices that are capable of emitting sound with one or more speakers, such as for entertainment purposes. Some such systems are configured for electronic communications. Many such systems include a microphone for sensing sound so as to serve as part of hands-free system such as for telephone calls, such as when the system is wirelessly coupled to another communications device (e.g., smart speakers). Such vehicle devices may support voice commands using virtual assistants that process received verbal commands and respond with audio output.

It would be desirable to have methods for monitoring bio-motion (i.e., physiological movement) in an efficient, effective manner in-vehicle. The realization of such a system and method would address a considerable technical challenge.

3 BRIEF SUMMARY OF THE TECHNOLOGY

The present technology concerns systems, methods, and apparatus for detecting movement of a subject, for example, while the subject is awake or asleep. Based on such movement detection, including for example breathing movement, the subject's movements, sleep related characteristics, respiratory characteristics, cardiac characteristics, sleep state, etc. may be detected. More particularly, an application associated with an electronic device including, for example, processor-enabled equipment, such as a vehicle audio device, in-car entertainment (ICE) device, in-vehicle infotainment (IVI) device or other processing device, such as a smartphone, tablet, smart speaker, guidance (GPS) device, or other hand-held processing device etc. It is clear from the provided examples that the scope of the expression "device", as well as the meaning of "system" used here, is not necessarily limited to a single piece of hardware. Any of these terms can encompass a single device, as well as one or more distinct devices. Some or all of these could be integrated in a single piece of equipment, or located separately and remotely from each other. The "device" or "system" is capable of transmitting and/or sensing reflected signals, such as with one or more transmitters and/or sensor(s) (i.e. speaker(s), microphone(s), infrared sensors, radio frequency transmitter/receiver etc.) being either integrated, and/or externally connectable) to detect physiological movement.

Some versions of the present technology may include a processor-readable medium, having stored thereon processor-executable instructions which, when executed by a processor, cause the processor to determine physiological parameters such as physiological movement of a user. Physiological movement may include any one or more of respiration movement, cardiac movement, limb movement (e.g., arm or leg), gesture movement and gross body movement. Apart from the physiological movement, which is a parameter that is derived from at least the detected reflected signal, physiological parameters may also include one or more characteristics that can be further derived from the derived physiological movement (e.g., respiratory amplitude, relative respiratory amplitude, respiratory rate, respiratory rate variability, derived from the respiratory movement signal; relative cardiac amplitude, cardiac amplitude, cardiac rate, cardiac rate variability, derived from the cardiac movement signal, etc.), as well as other characteristics (e.g., (a) presence state (present or absent); (b) sleep state (such as, awake or asleep); (c) sleep stage such as N-REM 1 (non-REM light sleep sub-stage 1), N-REM 2 (non-REM light sleep sub-stage 2), N-REM 3 (non-REM deep sleep (also referred to as slow wave sleep (SWS))), REM sleep etc.; or other sleep-related parameters such as (d) fatigue and/or (e) sleepiness; etc.). The processing device may be integrated with a vehicle (e.g., its cabin) or otherwise be portable or adapted to be inserted into the vehicle cable. The processor-executable instructions may comprise instructions to control producing, such as via a speaker coupled to a vehicular audio device or other sensor, a sensing or sound signal within an in-vehicle or cabin vicinity that may include a user. Whilst most of the described examples are applicable to the inside of the vehicle's cabin, similar sensing principles and considerations are applicable to the immediate vicinity on the outside of the vehicle. The processor-executable instructions may comprise instructions to control sensing, such as via a microphone coupled to the vehicular audio processing device or other sensor, a reflected signal or sound signal reflected from the user in the cabin vicinity of the vehicle. The processor-executable instructions may comprise instructions to process the sensed sound or reflected signal. The processor-executable instructions may comprise instructions to evaluate, via the microphone coupled to the vehicular audio device, a sensed audible verbal communication. The processor-executable instructions may comprise instructions to derive a physiological movement signal with the sensing or sound signal and the reflected signal or reflected sound signal. The processor-executable instructions may comprise instructions to generate, such as in response to the sensed audible verbal communication, an output based on an evaluation of the derived physiological movement signal.

Some versions of the present technology may include a processor-readable medium having stored thereon processor-executable instructions which, when executed by a processor of an electronic device, cause the processor to process data sensed in a cabin vicinity of a vehicle, to detect physiological movement of a user. The processor-executable instructions may include instructions to control producing a sensing signal in the cabin vicinity of a vehicle, such as a vehicle housing the electronic device. The processor-executable instructions may include instructions to control sensing, with a sensor, a reflected signal from the cabin vicinity of the vehicle. The processor-executable instructions may include instructions to derive a physiological movement signal with at least a portion of the sensed reflected signal and a signal representative of a portion of the sensing signal. The processor-executable instructions may include instructions to generate an output based on an evaluation of at least a portion of the derived physiological movement signal.

In some versions, the sensing signal may be any one or more of a radio frequency sensing signal generated by a radio frequency transmitter coupled with the electronic device, an acoustic sensing signal generated by a speaker coupled with the electronic device, and an infrared sensing signal generated by an infrared emitter coupled with the electronic device. The signal representative of the portion of the sensing signal may include an internally generated oscillator signal or a direct path measured sound signal. The instructions to derive the physiological movement signal derive may be configured to derive the physiological movement signal (a) with the sensing signal and the reflected signal; or (b) with the reflected signal and an associated signal that is associated with the sensing signal, optionally wherein the associated signal is an internally generated oscillator signal or a direct path measured signal.

The instructions to derive the physiological movement signal may be configured to multiply an oscillator signal with the portion of the sensed reflected signal. The derived physiological movement signal may include one or more of a respiratory motion, gross motion or a cardiac motion of a user within the cabin vicinity. The evaluation of the derived physiological movement signal may include determining any one or more of breathing rate, amplitude of breathing, relative amplitude of breathing, cardiac rate, cardiac amplitude and relative cardiac amplitude. The processor-executable instructions may include instructions to sense vehicle characteristics based on a signal from one or more vehicle sensors and generate the output based on the sensed vehicle characteristics. The processor-executable instructions may include instructions to sense vehicle characteristics based on a signal from one or more vehicle sensors, and to adjust at least a portion of the produced sensing signal based on the sensed vehicle characteristics.

In some versions, the sensed vehicle characteristics may include any one or more of vehicle speed, door opening state, window opening state, engine revolutions, vehicle location, seat occupancy, seatbelt fastening state, seat position, steering wheel grip status, steering wheel angle, air conditioning system status, fan setting, brake setting, gas pedal setting, cabin light, cabin noise, and/or cabin temperature. The processor-readable medium may include further comprising processor-executable instructions to evaluate, via a microphone coupled to the electronic device, a sensed audible verbal communication; and wherein the generated output based on an evaluation of the derived physiological movement signal is further based on the sensed audible verbal communication. The electronic device may comprise an audio entertainment system, wherein the sensing signal may be combined with an audio entertainment content signal, and wherein the combined sensing signal and audio entertainment content signal may be produced by one or more speakers of the audio entertainment system. At least a portion of the produced sensing signal may be a sound signal in a substantially inaudible sound range. The sound signal may be a low frequency ultrasonic acoustic signal. The sound signal may be a dual tone frequency modulated continuous wave signal. The dual tone frequency modulated continuous wave signal may comprise a first sawtooth frequency change at least partially overlapped with a second sawtooth frequency change in a repeated waveform.

The audio entertainment system may include a plurality of speakers and wherein the electronic device may be configured to derive different physiological movement signals, each derived physiological movement signal being associated with a different speaker of the plurality of speakers. The instructions to control producing a sensing signal may produce sensing signals in different sensing frequency ranges for each different speaker of the plurality of speakers. The instructions to control sensing the reflected signal from the cabin vicinity of the vehicle, may control sensing of reflected signals by using a plurality of microphones. The medium may further include processor-executable instructions to control the electronic device generate, with a speaker, a sound presentation to either discourage or promote sleep by the user in the cabin vicinity. The sound presentation may include a breathing entrainment exercise.

The electronic device may comprise a vehicle navigation system. The processor executable-instructions of the electronic device may be configured to, based on the output from the evaluation of the derived physiological movement signal, set a parameter for a navigation route provided with the vehicle navigation system. The electronic device may comprise a semi-autonomous or autonomous vehicle operations control system. The processor executable-instructions of the electronic device may be configured to, based on the output from the evaluation of the derived physiological movement signal, control any one or more of: movement of the vehicle, adjustment of a light condition of the cabin vicinity, adjustment of electrochromic glass transparency, movement of a seat of the cabin vicinity, adjustment of a braking parameter, adjustment of an acceleration parameter, adjustment of a suspension setting, adjustment of window coverage, adjustment of an acoustic barrier, immobilization of the vehicle, engagement of vehicle ventilation and/or engagement of vehicle cabin cooling/heating system. The evaluation of the derived physiological movement signal may include detection of any one or more of sleepiness, fatigue state, a sleep stage and a time in a sleep stage and/or a calculation of sleep score. The evaluation of the portion of the derived physiological movement signal may include detection of any one any of a sleep score, a sleep stage and a time in a sleep stage. The evaluation of the portion of the derived physiological movement signal by the electronic device may include a sleep service.

In some versions, the evaluation of the portion of the derived physiological movement signal by the electronic device may include a health screening service. Optionally, the health screening service may include any one or more of detection of respiratory health, detection of sleep disordered breathing, and detection of cardiac health. The evaluation of the portion of the derived physiological movement signal comprises detection of a gesture. The evaluation of the portion of the derived physiological movement signal by the electronic device may include detection of one or more of respiratory health related parameters, sleep disordered breathing related parameters, and/or cardiac health related parameters.

In some versions, the processor-readable medium may include processor-executable instructions to generate an ultra-wide band (UWB) sound sensing signal as audible white noise. The processor-readable medium may include processor executable instructions to detect user motion with the UWB sound signal. The medium may further include processor-executable instructions to generate, in a setup process, probing signals to map distances within the cabin vicinity. The medium may further include processor-executable instructions to detect presence or absence of a user in the cabin vicinity based on the portion of the derived physiological movement signal. The medium may further include processor-executable instructions to conduct biometric recognition of a user in the cabin vicinity based on the portion of the derived physiological movement signal. Optionally, the output may include a generated alert. The medium may further include processor-executable instructions to control enabling and disabling a vehicle operations control system of the vehicle based the biometric recognition. The medium may include processor-executable instructions to conduct biometric recognition of a user in the cabin vicinity based on the portion of the derived physiological movement signal. The output may be based on the biometric recognition and may include at least one of: (a) generating an alert; and (b) controlling enabling and disabling a vehicle operations control system of the vehicle. The medium may further include comprising processor-executable instructions to filter a sound signal sensed by a microphone coupled to the electronic device. The filter may be configured to mitigate or attenuate vehicular sounds. The vehicular sounds may include one or more of: motor noise, wind noise, a car horn, a door closing, and infotainment sounds.

In some versions, the evaluation of the portion of the derived physiological movement signal by the electronic device may include classification of the derived physiological movement signal, wherein the classification evaluates features determined from the portion of the derived physiological movement signal by a deep belief network. The evaluation of the derived physiological movement signal by the electronic device may include determination of a child remaining alone in the cabin vicinity, and wherein the output comprises a generated warning. The output may further include a control signal to activate a vehicle operations control system based on the determination of a child remaining alone in the cabin vicinity. Optionally, the vehicle operations control system may include a vehicle environment control system and the control signal may initiate a ventilation and/or temperature condition of the cabin vicinity provided by the vehicle environment control system. The evaluation of the portion of the derived physiological movement signal by the electronic device may include a determination of a child remaining alone in the cabin vicinity, wherein the output may include: (a) a generated warning, or (b) the vehicle operations control system initiating a ventilation and/or temperature condition of the cabin vicinity.

In some versions, the medium may further include processor-executable instructions to record data based on the derived physiological movement signal in a blockchain data system. The medium may further include processor-executable instructions to generate the output as an interactive language process through a chatbot program. The electronic device may comprise a hand-held processing device. The electronic device may include one or more integrated components of a vehicle or a vehicular processing device. In some versions, one or both of (a) the sensor and (b) a component configured to produce the sensing signal, may be an integrated component(s) of a vehicle.

Some versions of the present technology may include a server with access to the processor-readable medium as described herein. The server may be configured to receive requests for downloading the processor-executable instructions of the processor-readable medium to an electronic device or a vehicular processing device over a network.

Some versions of the present technology may include an electronic device. The electronic device may comprise one or more processors arranged to be coupled to a sensor operating in a cabin vicinity of a vehicle; and (a) any processor-readable medium as described herein, or (b) a processor-readable medium configured to access the processor-executable instructions of any server described herein. The sensor may comprise at least one of (a) a speaker and microphone, (b) an infrared emitter and detector, or (c) a radio frequency transceiver. The electronic device may include any one of more of an audio entertainment system, a vehicle navigation system, and a semi-autonomous or autonomous vehicle operations control system. The electronic device may include one or more integrated components of a vehicle or a vehicular processing device. The electronic device may further comprise the vehicle. The electronic device may include at least one portable component. The portable component may include a smart phone, a smart watch or smart jewelry.

Some versions of the present technology may include a method of a server having access to any processor-readable medium described herein, or to the electronic device described herein. The method may include receiving, at the server, a request for downloading the processor-executable instructions of the processor-readable medium to the electronic device over a network; and transmitting the processor-executable instructions to the electronic device in response to the request.

Some versions of the present technology may include a method of a processor of an electronic device. The method may include accessing, with the processor, any of the processor-readable medium(s) described herein. The method may include executing, in the processor, the processor-executable instructions of the processor-readable medium.

Some versions of the present technology may include a method of one or more processors of an electronic device to detect physiological movement of a user in a cabin vicinity of a vehicle. The method may include controlling producing a sensing signal in the cabin vicinity of the vehicle. The method may include controlling sensing, with a sensor, a reflected signal from the cabin vicinity of the vehicle. The method may include deriving a physiological movement signal with at least a portion of the sensed reflected signal and a signal representative of a portion of the sensing signal. The method may include generating an output based on an evaluation of at least a portion of the derived physiological movement signal.

In some versions of the method the sensing signal may be any one or more of a radio frequency sensing signal generated by a radio frequency transmitter coupled with the electronic device, an acoustic sensing signal generated by a speaker coupled with the electronic device, and an infrared sensing signal generated by an infrared emitter coupled with the electronic device. The signal representative of the portion of the sensing signal may include an internally generated oscillator signal or a direct path measured signal. The method may include deriving the physiological movement signal (a) with the sensing signal and the sensed reflected signal; or (b) with the sensed reflected signal and an associated signal that is associated with the sensing signal, optionally wherein the associated signal is an internally generated oscillator signal or a direct path measured signal. The method may include deriving the physiological movement signal comprises multiplying an oscillator signal with the portion of the sensed reflected sound signal. The derived physiological movement signal may include one or more of a respiratory motion, a cardiac motion, or gross motion, of a user within the cabin vicinity. The evaluation of the portion of the derived physiological movement signal may include determining any one or more of breathing rate, relative amplitude of breathing, amplitude of breathing, cardiac rate, relative cardiac amplitude, and cardiac amplitude. The method may include sensing vehicle characteristics based on a signal from one or more vehicle sensors and generating the output based on the sensed vehicle characteristics. The method may include sensing vehicle characteristics based on a signal from one or more vehicle sensors, and to adjust at least a portion of the produced sensing signal based on the sensed vehicle characteristics. The sensed vehicle characteristics may include any one or more of vehicle speed, door opening state, window opening state, engine revolutions, vehicle location, seat occupancy, seatbelt fastening state, seat position, steering wheel grip status, steering wheel angle, air conditioning system status, fan setting, brake setting, gas pedal setting, cabin light, cabin noise, and/or cabin temperature.

The method may include further evaluating, via a microphone coupled to the electronic device, a sensed audible verbal communication; and wherein the generated output based on an evaluation of the portion of the derived physiological movement signal is further based on the sensed audible verbal communication. The electronic device may include an audio entertainment system and the method may include combining the sensing signal with an audio entertainment content signal, and producing the combined sensing signal and audio entertainment content signal by one or more speakers of the audio entertainment system. At least a portion of the produced sensing signal may be a sound signal in a substantially inaudible sound range. The sound signal may be a low frequency ultrasonic acoustic signal. The sound signal may be a dual tone frequency modulated continuous wave signal. The dual tone frequency modulated continuous wave signal comprises a first sawtooth frequency change at least partially overlapped with a second sawtooth frequency change in a repeated waveform. The electronic device may include an audio entertainment system that may include a plurality of speakers and wherein the electronic device derives different physiological movement signals, each derived physiological movement signal being associated with a different speaker of the plurality of speakers.

In some versions, the controlling producing a sensing signal produces sensing signals in different sensing frequency ranges for each different speaker of the plurality of speakers. The controlling sensing the reflected signal from the cabin vicinity of the vehicle may include controlling sensing of reflected signals by using a plurality of microphones. The method may include controlling the electronic device to generate, with a speaker, a sound presentation to either discourage or promote sleep by the user in the cabin vicinity. The sound presentation may include a breathing entrainment exercise. The electronic device may include a vehicle navigation system. The electronic device, based on the output from the evaluation of the portion of the derived physiological movement signal, may set a parameter for a navigation route provided with the vehicle navigation system.

The electronic device may include a semi-autonomous or autonomous vehicle operations control system. The electronic device may control, based on the output from the evaluation of the derived physiological movement signal, any one or more of: movement of the vehicle, adjustment of a light condition of the cabin vicinity, adjustment of electrochromic glass transparency, movement of a seat of the cabin vicinity, adjustment of a braking parameter, adjustment of an acceleration parameter, adjustment of a suspension setting, adjustment of window coverage, adjustment of an acoustic barrier, immobilization of the vehicle, engagement of vehicle ventilation and/or engagement of vehicle cabin cooling/heating system. The evaluation of the portion of the derived physiological movement signal may include detecting any one or more of sleepiness, fatigue state, a sleep stage and a time in a sleep stage and/or a calculation of sleep score. The evaluation of the portion of the derived physiological movement signal may include detecting any one of a sleep score, a sleep stage and a time in a sleep stage. The evaluation of the portion of the derived physiological movement signal by the electronic device may include a sleep service. The evaluation of the portion of the derived physiological movement signal by the electronic device may include a health screening service, and optionally wherein the health screening service detects any one or more of respiratory health, sleep disordered breathing, and cardiac health. The evaluation of the portion of the derived physiological movement signal may detect a gesture. The evaluation of the portion of the derived physiological movement signal by the electronic device may include detection of any one or more of respiratory health related parameters, sleep disordered breathing related parameters, and cardiac health related parameters.

The produced sensing signal may include ultra-wide band (UWB) sound sensing signal generated as audible white noise. The method may further include generating an ultra-wide band (UWB) sound sensing signal as audible white noise, and detecting user motion with the UWB sound signal. The method may include generating, in a setup process, probing signals to map distances within the cabin vicinity. The method may further include detecting presence and absence of a user in the cabin vicinity based on the derived physiological movement signal. The method may further include conducting biometric recognition of a user in the cabin vicinity based on the derived physiological movement signal. Optionally, the output may include a generated alert. The method may further include controlling enabling and disabling a vehicle operations control system of the vehicle based the biometric recognition. The output may be based on the biometric recognition and may include at least one of (i.e., or both): (a) generating an alert and (b) controlling enabling and disabling a vehicle operations control system of the vehicle. The method may further include filtering a sound signal sensed by a microphone coupled to the electronic device, the filtering may be configured to mitigate or attenuate vehicular sounds. Optionally, the vehicular sounds may include one or more of: motor noise, wind noise, a car horn, a door closing, and infotainment sounds.

The evaluation of the derived physiological movement signal by the electronic device may include classifying the derived physiological movement signal, wherein the classifying evaluates features determined from the derived physiological movement signal by a deep belief network. The evaluation of the derived physiological movement signal by the electronic device may include determining presence of a child remaining alone in the cabin vicinity, and wherein the output comprises a generated warning. The output may include a control signal to activate a vehicle operations control system based on the determining presence of a child remaining alone in the cabin vicinity. The evaluation of the portion of the derived physiological movement signal by the electronic device may include determining a presence of a child remaining alone in the cabin vicinity, and the output may include: (a) a generated warning, or (b) the vehicle operations control system initiating a ventilation and/or temperature condition of the cabin vicinity provided by the vehicle environment control system. Optionally, the vehicle operations control system may include a vehicle environment control system and the control signal may initiate a ventilation and/or temperature condition of the cabin vicinity provided by the vehicle environment control system. The method may further include recording data based on the derived physiological movement signal in a blockchain data system. The method may further include generating the output as an interactive language process through a chatbot program. The electronic device may include, or be, a handheld processing device. The electronic device may include one or more integrated components of a vehicle or a vehicular processing device. One or both of (a) the sensor and (b) a component configured to produce the sensing signal, may be an integrated component(s) of a vehicle.

The methods, systems, devices and apparatus described herein can provide improved functioning in a processor, such as of a processor of an in-vehicle audio and/or processing device, a general or specific purpose computer, portable computer processing device (e.g., mobile phone, tablet computer, smart speaker, smart television etc.), respiratory monitor and/or other processing apparatus utilizing a motion sensor such as a microphone and speaker. Moreover, the described methods, systems, devices and apparatus can provide improvements in the technological field of automated vehicle audio apparatus.

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

4 BRIEF DESCRIPTION OF THE DRAWINGS

The present technology is illustrated by way of example, and not by way of limitation, in the figures of the accompanying drawings, in which like reference numerals refer to similar elements including:

5 DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing particular examples discussed and is not intended to be limiting.

The following description is provided in relation to various forms of the present technology that may share common characteristics or features. It is to be understood that one or more features of any one exemplary form may be combinable with one or more features of another form. In addition, any single feature or combination of features in any of form described herein may constitute a further exemplary form.

5.1 Screening, Monitoring, and Detection with In-Vehicle Equipment

The present technology concerns physiological sensing systems, methods, and apparatus for detecting movement of a subject, including, for example, gross body movement, breathing movement and/or cardiac related chest movement, such as while the subject is in a vehicular environment. More particularly, the technology concerns processing applications associated with in-vehicle motion sensing device(s), such as for an automobile entertainment system. In some versions the sensing device may be a smartphone, a guidance system, an in-car audio system, a tablet, a mobile device, a mobile phone, a smart television, a laptop computer, etc. that uses the device sensors, such as a speaker and microphone, to detect such in-vehicle motion. Such an electronic device system may include a portable component, such as a smart phone, smart watch, and/or smart jewelry.

Figure 1:
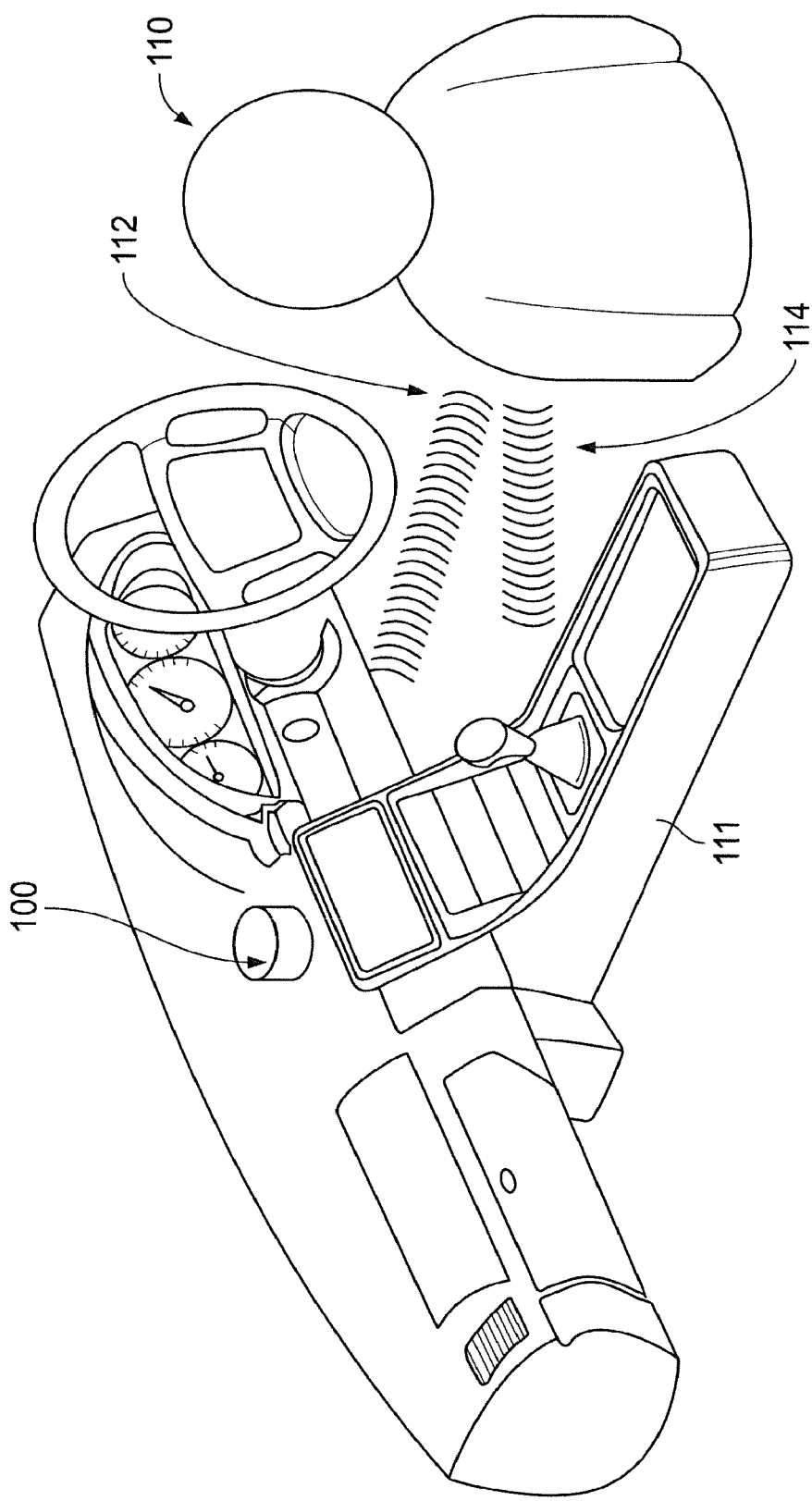
FIG. 1 illustrates an example in-vehicle motion sensing device, such as one using low frequency ultrasonic biomotion sensing, with signal generation and processing techniques described herein.
Figure 2:
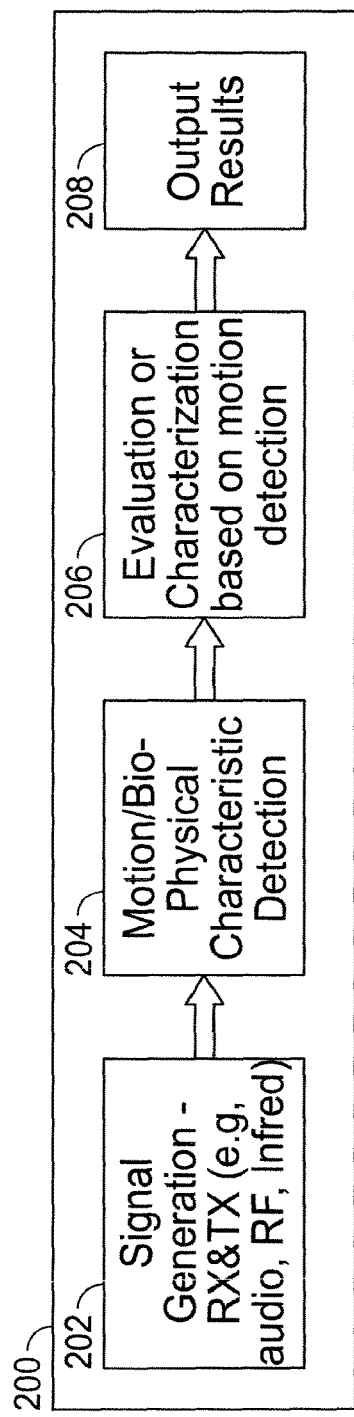
FIG. 2 illustrates an example processing device for receiving audio information from an in-vehicle vicinity of the device and a schematic illustration of example processes of the device.
Figure 2:
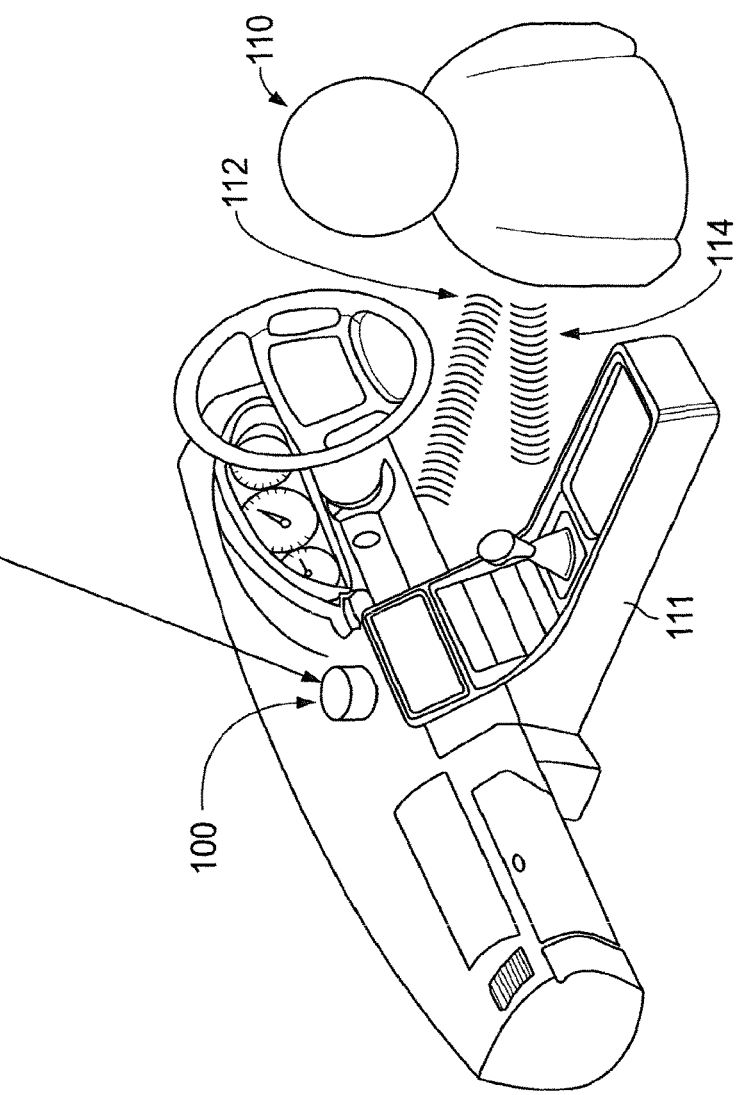

A particularly minimalist or non-obtrusive version of an example system suitable for implementing the present technology is now described with reference to FIGS. 1 to 3. The in-vehicle audio device may be implemented as a processing device 100 having one or more processors, such as a microcontroller, that may be a smart speaker that is configured with an application 200 for detecting movement of subject 110. It may be placed within a vehicle 111 or otherwise integrated with components of a cabin (e.g., audio system, dashboard, doors, seats etc.) of a vehicle 111 near subject 110. Optionally, processing device 100 may be, for example, a smartphone, tablet computer, laptop computer, smart speaker, smart television or other electronic device. The processor(s) of the processing device 100 may be configured to, among other things, execute the functions of application 200, including causing a sensing signal 112, such as an acoustic or audio signal, to be generated and transmitted, typically through the air in a generally restricted vicinity of a vehicle. The processing device may receive a reflection 114 of the transmitted signal by sensing it with, for example, a transducer such as a microphone. The processing device may process the sensed signal, such as by demodulation with the transmitted signal, to determine body movement such gross body movement, limb movement, cardiac movement and respiration movement. Processing device 100 will may comprise, among other components, a speaker and a microphone. The speaker may be implemented to transmit the generated audio signal and the microphone to receive the reflected signal. The generated audio signal for sensing and processing may be implemented with any of the techniques described in International Patent Application PCT/EP2017/073613 filed on Sep. 19, 2017, the entire disclosure of which is incorporated herein by reference.

While the sensing apparatus are generally described herein in relation to acoustic sensing (e.g., low frequency ultrasonic sensing), it is understood that the methods and devices may be implemented using other sensing techniques. For example, as an alternative, the processing device may be implemented with a radio frequency transceiver of an RF sensor to serve as sensing apparatus, such that the generated signal and reflected signal are RF signals. Such a RF sensing device, which may be integrated with or coupled to the processing device, may implemented with any of the techniques and senor components described in International Patent Application No. PCT/US2013/051250, entitled "Range Gated Radio Frequency Physiology Sensor" and filed on Jul. 19, 2013; International Patent Application No. PCT/EP2017/070773, entitled "Digital Radio Frequency Motion Detection Sensor" and filed on Aug. 16, 2017; and International Patent Application No. PCT/EP2016/069413, entitled "Digital Range Gated Radio Frequency Sensor" and filed on Aug. 16, 2017. Similarly, in alternative versions, such sensing apparatus for the transmission of a sensing signal and sensing of its reflection may be implemented with an infrared radiation generator and an infrared radiation detector (e.g., an IR emitter and IR detector). The processing of such signals for motion detection and characterization as described herein may be similarly implemented.

Using a combination of two or more of these different sensing techniques, can enhance the sensing outcome by combining the advantages of the respective techniques. For instance, the discussed acoustic sensing technique is quite acceptable in the noisy environment of, for example, city driving or higher engine revolutions/vehicle speeds. However, a user with very sensitive hearing may find the use of this technique to be problematic, such as during country driving or at lower engine revolutions/vehicle speeds, when the noise is much lower and the sensing signal is easier to hear. Similarly, whilst an IR sensing provides a good S/N signal during night time, its use may be problematic in the light (and heat) of day. An IR sensing may be used in this case at night, complemented by the use of the acoustic sensing during the day.

Optionally, the sensing methodologies of the processing device may be implemented with sensing apparatus in or by other types of devices such as a travel/portable sleeping therapy device (e.g., a travel/portable respiratory therapy device such as a continuous positive airway pressure (e.g., "CPAP") device or high flow therapy device) (not shown) where the therapy device serves as the processing device 100 or works in conjunction with a separate processing device 100. Examples of such devices, including a pressure device or blower (e.g., a motor and impeller in a volute), one or more sensors and a central controller of the pressure device or blower, may be considered in reference to the devices described in International Patent Publication No. WO/2015/061848 (Appl. No. PCT/AU2014/050315) filed on Oct. 28, 2014, and International Patent Publication No. WO/2016/145483 (Appl. No. PCT/AU2016/050117) filed on Mar. 14, 2016, the entire disclosures of which are incorporated herein by reference. Such a respiratory therapy device may include an optional humidifier 4000 and provide therapy to a patient interface via a patient circuit (e.g., a conduit). In some cases, the respiratory therapy device might have a separate sensor, such as a microphone, for sensing internal sound-related conditions within and through the patient circuit, as opposed to serving to sense the externally sound related acoustic conditions of the processes described throughout this application.

Processing device 100 may be adapted to provide an efficient and effective method of monitoring a subject's breathing and/or other movement related characteristics. When used within a vehicle, such as during sleep, the processing device 100 and its associated methods can be used to detect, for example, the user's breathing and identify sleep stages, sleep states, transitions between states, breathing and/or other respiratory characteristics. When used during wake, the processing device 100 and its associated methods can be used to detect movement such as presence or absence of a person or subject breathing (inspiration, expiration, pause, and derived rate), sleepiness and/or fatigue, a ballistocardiogram waveform and/or subsequent derived heart rate, etc. Such movement or movement characteristics may be used for controlling various functions as described herein in more detail.

Processing device 100 may include integrated chips, a memory and/or other control instruction, data or information storage medium. For example, programmed instructions encompassing the assessment/signal processing methodologies described herein may be coded on integrated chips in the memory of the device or apparatus to form an application specific integrated chip (ASIC). Such instructions may also or alternatively be loaded as software or firmware using an appropriate data storage medium. Optionally, such processing instructions may be downloaded such as from a server over a network (e.g. an internet) to the processing device such that when the instructions are executed, the processing device serves as a screening or monitoring device.

Figure 3:
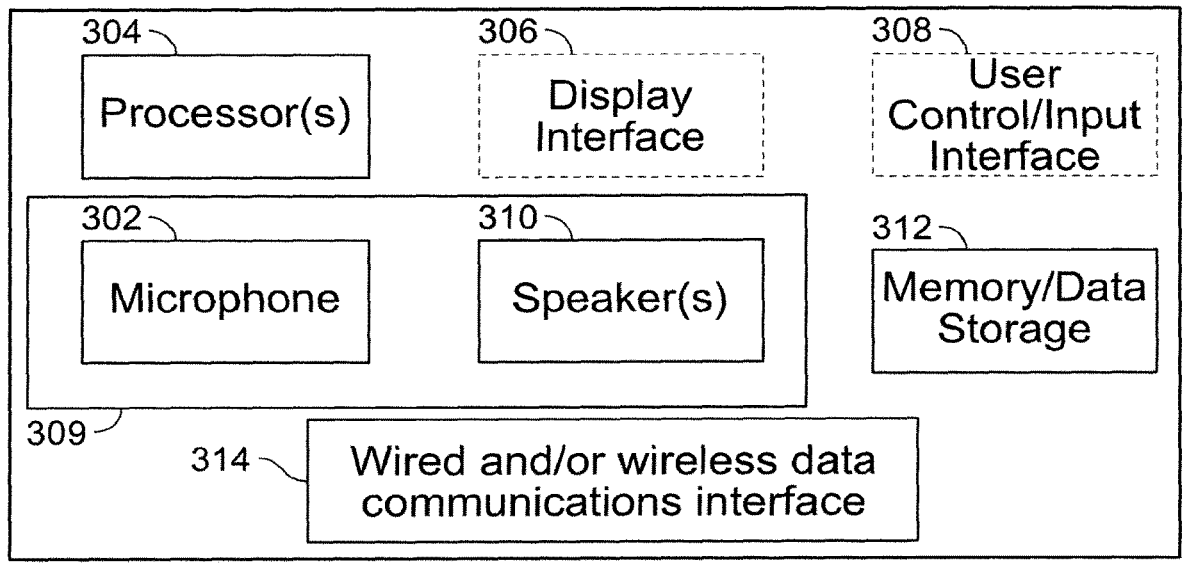
FIG. 3 is schematic illustration of a processing device, such as a smart audio device, as it may be configured in accordance with some forms of the present technology.

Accordingly, processing device 100 may include a number of components as illustrated by FIG. 3. The processing device 100 may include, among other components, sensing apparatus 309, such as a microphone(s) or sound sensor 302 and a speaker 310 for acoustic sensing, a processor(s) 304, an optional display interface 306, an optional user control/input interface 308, and a memory/data storage 312, such as with the processing instructions of the processing methodologies/modules described herein. In some cases, the microphone and/or speaker may serve as the user interface with the processor(s) of the device, such as to control operations of the processing device, for example, when the processing device responds, such as via the speaker, to audio and/or verbal commands sensed by the microphone. In this regard, the processing device 100 may serve as a voice assistant such as using natural language processing.

One or more of the components of processing device 100 may be integral with or operably coupled with processing device 100. For example, sensing apparatus 309 (e.g., microphone(s) or sound sensor 302 and speaker 310) may be integral with processing device 100 or coupled with processing device 100 such as through a wired or wireless link (e.g., Bluetooth, Wi-Fi etc.). Thus, the processing device 100 may include a data communications interface 314.

Memory/data storage 312 may comprise a plurality of processor control instructions for controlling processors 304. For example, memory/data storage 312 may comprise processor control instructions for causing application 200 to be performed by the processing instructions of the processing methodologies/modules described herein.

Examples of the present technology may be configured to use one or more algorithms or processes, which may be embodied by application(s) 200, to detect motion, breathing, and optionally sleep characteristics while a user is asleep using the processing device 100. For example, application 200 may be characterized by several sub-processes or modules. As shown in FIG. 2, application 200 may include a sensing signal generation and transmission sub-process 202, a motion and bio-physical characteristic detection sub-process 204, a motion characterization sub-process 206 such as for subject absence/presence detection, biometric identification, fatigue, sleepiness, sleep characterization, respiratory or cardiac related characterizations etc., and a results output sub-process 208, such as for presenting information or controlling various devices as described in more detail herein.

For example, optional sleep staging at processing 206, such as in a sleep staging processing module may be implemented. However, any one or more of such processing modules/blocks may optionally be added (e.g., sleep scoring or staging, subject recognition processing, fatigue recognition, sleepiness recognition, presence absence recognition, biometric identification of a person (biometric recognition), motion monitoring and/or prediction processing, appliance control logic processing, or other output processing, etc.). In some cases, the functions of signal post-processing 206 may be performed using any of the components, devices and/or methodologies of the apparatus, system and method described in any of the following patents or patent applications, wherein the entire disclosures of each is incorporated by reference herein: International Patent Application No. PCT/US2007/070196, filed Jun. 1, 2007 and entitled "Apparatus, System, and Method for Monitoring Physiological Signs;" International Patent Application No. PCT/US2007/083155, filed Oct. 31, 2007, entitled "System and Method for Monitoring Cardio-Respiratory Parameters;" International Patent Application No. PCT/US2009/058020, filed Sep. 23, 2009, entitled "Contactless and Minimal-Contact Monitoring of Quality of Life Parameters for Assessment and Intervention;" International Application No. PCT/US2010/023177, filed Feb. 4, 2010, entitled "Apparatus, System, and Method for Chronic Disease Monitoring;" International Patent Application No. PCT/AU2013/000564, filed Mar. 30, 2013, entitled "Method and Apparatus for Monitoring Cardio-Pulmonary Health;" International Patent Application No. PCT/AU2015/050273, filed May 25, 2015, entitled "Methods and Apparatus for Monitoring Chronic Disease;" International Patent Application No. PCT/AU2014/059311, filed Oct. 6, 2014, entitled "Fatigue Monitoring and Management System;" International Patent Application no. PCT/EP2017/070773, filed on Aug. 16, 2017, entitled "Digital Radio Frequency Motion Detection Sensor;" International Patent Application No. PCT/AU2013/060652, filed Sep. 19, 2013, entitled "System and Method for Determining Sleep Stage;" International Patent Application No. PCT/EP2016/058789, filed Apr. 20, 2016, entitled "Detection and Identification of a Human from Characteristic Signals;" International Patent Application No. PCT/EP2016/080267, filed on Dec. 8, 2016, entitled "Periodic Limb Movement Recognition with Sensors"; International Patent Application No. PCT/EP2016/069496, filed 17 Aug. 2016, entitled "Screener for Sleep Disordered Breathing;" International Patent Application No. PCT/EP2016/058806, filed on Apr. 20, 2016, "Gesture Recognition with Sensors"; International Patent Application No. PCT/EP2016/069413, filed Aug. 16, 2016, entitled "Digital Range Gated Radio Frequency Sensor;" International Patent Application No. PCT/EP2016/070169, filed Aug. 26, 2016, entitled "Systems and Methods for Monitoring and Management of Chronic Disease;", International Patent Application No. PCT/US2014/045814, filed Jul. 8, 2014, entitled "Methods and Systems for Sleep Management;" U.S. patent application Ser. No. 15/079,339, filed Mar. 24, 2016, entitled "Detection of Periodic Breathing." Thus, in some examples, the processing of detected movement, including for example, the breathing movement, may serve as a basis for determining any one or more of (a) a sleep state indicating sleep; (b) a sleep state indicating awake; (c) a sleep stage indicating deep sleep; (d) a sleep stage(s) indicating light sleep (e.g., N1 or N2 simply light sleep); and (e) a sleep stage indicating REM sleep. In this regard, while the sound and/or infrared related sensing technologies of the present disclosure provide for different mechanisms/processes for motion sensing such as using a speaker and microphone and processing of the sound signals, when compared to radar or RF sensing technologies as described in some of these incorporated references, once a motion or breathing signal, such as breathing rate is obtained with the sound sensing/processing methodologies described in this specification) the principles of processing breathing or other physiological movement signals for an extraction of sleep states/stages information may be implemented by the determination methodologies of these incorporated references. For example, once the respiration rate and movement and activity counts are determined from motion whether by RF or SONAR, sleep staging is a common analysis. By way of additional example, the sensing wavelengths may be different between an RF pulsed CW and a SONAR FMCW implementation. Thus, velocity may be determined differently such as by detecting movement across a range (different sensing distances). For FMCW, movement detection may be made at multiple ranges. Thus, one or more moving targets may be tracked (whether it is two people, or indeed different parts of a person—depending on their angle with respect to the SONAR sensor).

Typically, an audio signal from a speaker, such as an in-vehicle audio entertainment/navigation or vehicle control system, may be generated and transmitted towards a user for sensing within a vehicle, such as an audio signal using one or more tones described herein. A tone provides pressure variation in the vehicle (e.g., air) at one or more particular frequencies. For purposes of this description, the generated tones (or audio signals or sound signals) may be referred to as "sound", "acoustic" or "audio" because they may be generated in a like manner to audible pressure waves (e.g., by a speaker). However, such pressure variations and tone(s) should be understood herein to be either audible or inaudible, notwithstanding their characterization by any of the terms "sound", "acoustic" or "audio." Thus, the audio signal generated may be audible or inaudible, wherein the frequency threshold of audibility across the human population varies by age. The signal may be substantially inaudible such that most people cannot discern the sound (e.g., in the range above 18 kHz). The typical "audio frequency" standard range is around 20 Hz to 20,000 Hz (20 kHz). The threshold of higher frequency hearing tends to reduce with age, with middle aged people often unable to hear sounds with frequencies above 15-17 kHz, whereas a teenager may be able to hear 18 kHz. The most important frequencies for speech are approximately in the range 250-6,000 Hz. Speaker and microphone signal responses for typical consumer smartphones, or in-vehicle audio equipment, may be designed to roll off above 19-20 kHz in many cases, with some extending to above 23 kHz and higher (especially where the device supports a sampling rate of greater than 48 kHz such as 96 kHz). Therefore, for most people, it is possible to use signals in the range of 17/18 to 24 kHz and remain inaudible. For younger people that can hear 18 kHz but not 19 kHz, a band of 19 kHz to say 21 kHz could be employed. It is noted that some domestic pets may be able to hear higher frequencies (e.g., dogs up to 60 kHz and cats up to 79 kHz). A suitable range for the sensing audio signal of the present technology may be in a low ultrasonic frequency range such as 15 to 24 kHz, 18 to 24 kHz, 19 to 24 kHz, 15 to 20 kHz, 18 to 20 kHz or 19 to 20 kHz.

Any of the arrangements and methods of audio sensing, such as with use of low frequency ultrasonic sensing signals, as described in PCT/EP2017/073613 may be implemented by the processing device described herein. However, in some cases, a dual tone FMCW (also referred to as a dual ramp technology) may be implemented as described herein.

Figure 4A:
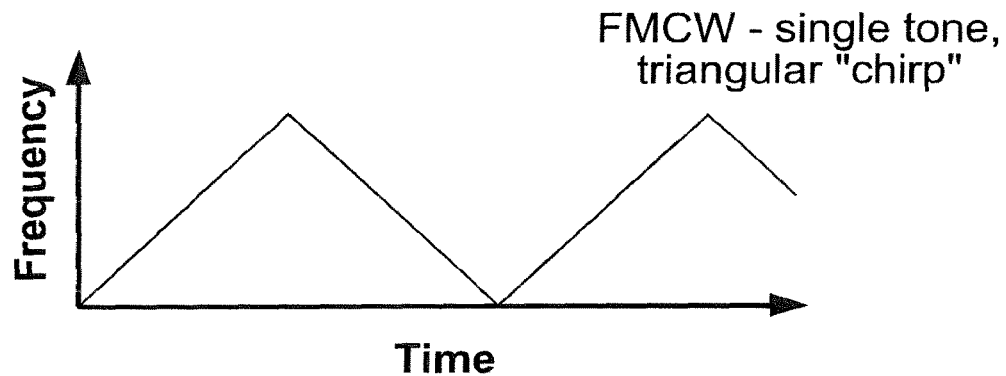
FIG. 4A shows frequency characteristics of a single tone chirp such as for frequency modulated continuous wave sensing (FMCW).

For example, a triangular FMCW waveform with one "tone" (i.e., that is swept up and down in frequency) may be generated by the processing device using its speaker(s) where the waveform has the frequency versus time characteristics illustrated in FIG. 4A, and where processing of the up-sweep, or just the down-sweep, or even both may be evaluated for distance detection. The phase-continuous triangular form for one tone is highly desirable as it minimizes or removes any audible artefact in the played sound created by a phase discontinuity. A ramp variant of this can give rise to a very unpleasant and audible buzzing sound, as the speaker(s) is/are asked to jump from playing a certain amplitude sound at a frequency to a much lower (or much higher) frequency at a similar amplitude within the space of a sample; the mechanical change in the speaker can give rise to a click, and the frequent repetition of the chirp means that the user hears a buzz (many closely spaced clicks).

Figure 4B:
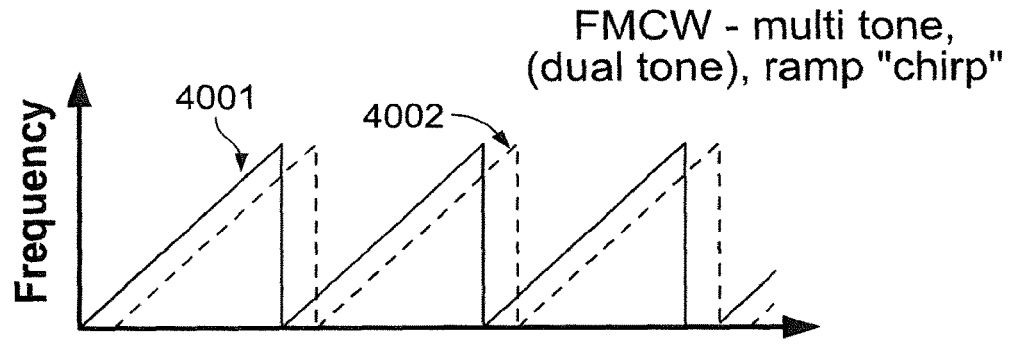
FIG. 4B shows frequency characteristics of a dual tone chirp such as for frequency modulated continuous wave sensing (FMCW).

Optionally, in some versions of the present technology, the sensing signal (e.g., acoustic) as a FMCW may be implemented with special dual "tones" with a ramp waveform (e.g. which consists of an up-sweep or a down-sweep only)—so that there is a sharp change in frequency from the end of one ramp (frequency ramp up and down) to the next (frequency ramp up and down) without audible artefact. Such a dual "tone" frequency modulated waveform showing its frequency characteristics relative to time, where at least two changing frequency ramps overlap during a period of time and these frequency ramps each may have a different frequency relative to the other(s) at any instant of time in the period such as for the duration of the ramping, is illustrated in FIG. 4B in relation to the dashed line versus the solid line. This can ultimately simplify the data processing in the system, and also remove the potentially high amplitude transition at each point of a triangular waveform. Sharp and repetitive transitions can sometimes trigger strange behavior in a system's low level DSP/CODEC/firmware.

FIGS. 4A and 4B show a frequency domain comparison of FMCW single tone (FIG. 4A) and dual tone (FIG. 4B) implementations. A single tone (FIG. 4A) may preferentially include a downsweep (a reduction in produced frequency over time) to ensure inaudibility. However, a downsweep may be omitted but may cause some audibility. A dual tone (tone pair) (FIG. 4B) can help avoid the need for such a downsweep, as the time domain representation is shaped such as to be inaudible. FIG. 4B shows the first tone 4001 and the optional second tone 4002 overlap. The figure does not show the received echo (i.e., the reflection signal). Thus, tones form a first sawtooth frequency change overlapped with a second sawtooth frequency change in a repeated waveform. They are continuous such that they may be repeated during a sensing period.

Thus, there are different ways that the acoustic sensing signal can be created when implementing a low frequency ultrasonic sensing system with an FMCW type of approach. This may involve differences in waveform shape in the frequency domain (e.g., triangular (symmetric or asymmetric), ramp, sinusoidal etc.), period (duration of the "chirp" in time), and bandwidth (frequency covered by the "chirp"— e.g., 19-21 kHz). It is also possible to use two or more simultaneous tones in an FMCW configuration.

The choice of number of samples defines a possible output demodulated sampling rate (e.g., 512 samples at a sampling rate of 48 kHz equates to 93.75 Hz (48,000/512), whereas a 4096 sample duration sweep time equates to 11.72 Hz (48,000/4096). If a triangular waveform is used with a 1500 sample uptime, and 1500 sample downtime, then the output sampling rate is 16 Hz (48,000/3000). For this type of system, synchronization can be performed by multiplying the signal by a reference template, for example.

Regarding the choice of the output sampling rate, empirical testing has shown that operating in the approximate region of 8 to 16 Hz is preferable, as it broadly avoids 1/f noise (low frequency effects due to air movement, potentially strong fading, and/or room modes) as well as staying out of the reverberation region seen at higher demodulated sampling rates (i.e., we have allowed time for the energy in any one frequency of sensing waveform "chirp" to fade before the next similar component in next "chirp"). Presented another way, if you make bins too wide, changes in airflow and temperature (e.g., opening door and heat goes in or out of room) means any block you are looking at could contain an unwanted baseline drift which can look like breathing. Practically, this means that a wave is seen to move across the band (across range bins) as the air moves. This is distinct from more localized effects from a desk or pedestal fan, or an air conditioning or other HVAC system. Effectively, if the blocks are made too wide, the system begins to "look like" a CW system. On the other hand, one can get reverb if the system works at too high a refresh rate (i.e., too short a ramp).

For a triangular FMCW waveform with one "tone" (i.e., that is swept up and down in frequency) as illustrated in FIG. 4A, a system can process, for example, just the up-sweep, or just the down-sweep, or indeed both may be processed for distance detection. The phase-continuous triangular form for one tone is highly desirable as it minimizes or removes any audible artefact in the played sound created by a phase discontinuity. A ramp variant of this can give rise to a very unpleasant and audible buzzing sound, as the speaker(s) is/are asked to jump from playing a certain amplitude sound at a frequency to a much lower (or much higher) frequency at a similar amplitude within the space of a sample; the mechanical change in the speaker can give rise to a click, and the frequent repetition of the chirp means that the user hears a buzz (many closely spaced clicks).

An important consideration to implemented such a dual tone signal is that the resulting shape is made (shaped) such that the speaker/system does not need to make a sharp transition, and it has zero points. This can reduce the need for filtering that would otherwise be implemented to render the signal inaudible. For example, high pass or band pass filtering may be avoided while still permitting the signal to operate as an inaudible sensing signal. The presence of zeros in the waveform eases signal processing because that the zeros simplifies synchronization of the transmit and the receiving of such a signal (e.g., for demodulation). A consequence of the dual tones is that it offers an element of fading robustness as more than one tone is used—and fading can vary with the frequency used, as well as phase or frequency (e.g., one might use a 100 Hz offset between the FMCW tones in a dual tone system).

Figure 7:
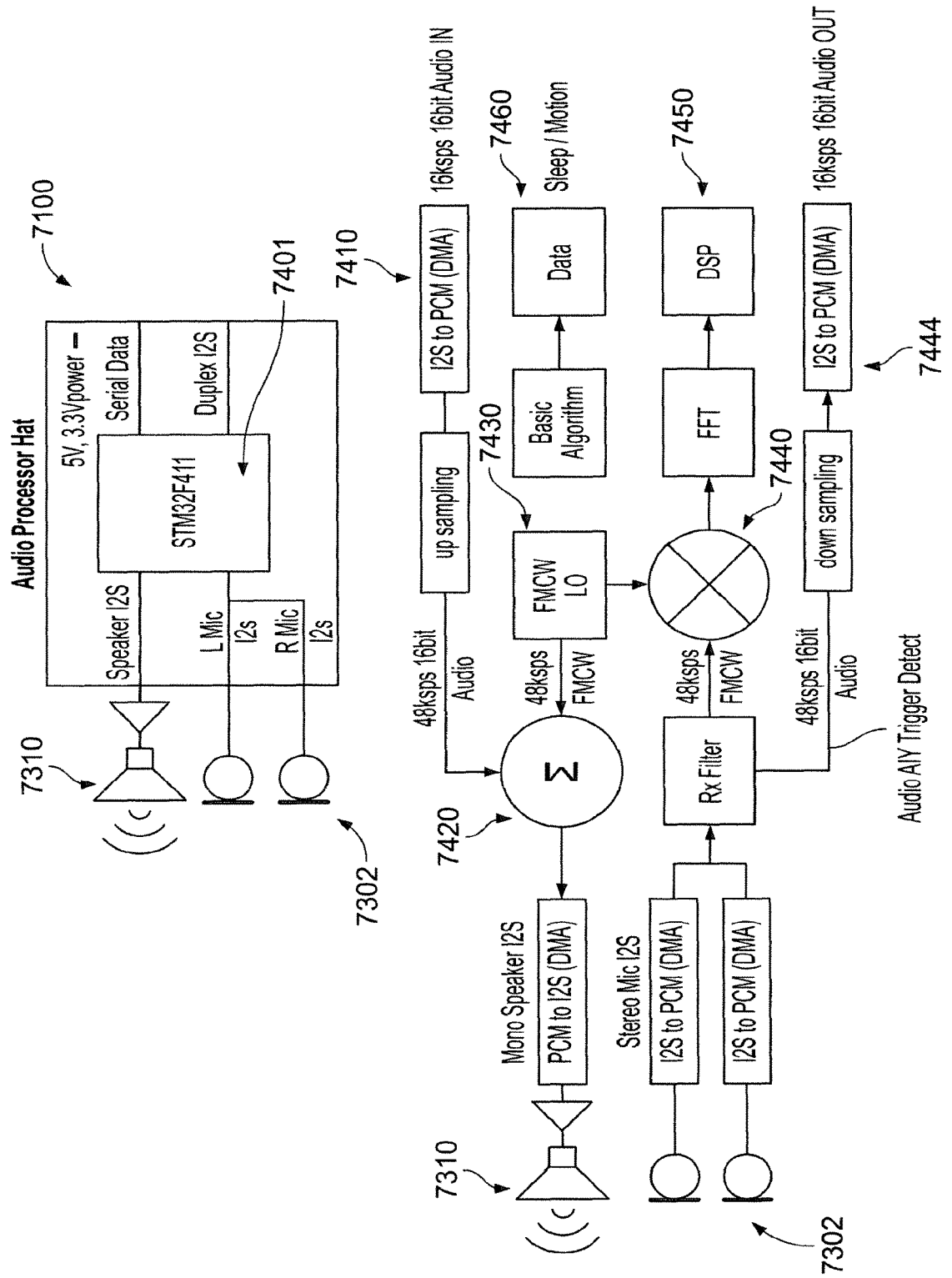
FIG. 7 illustrates example audio processing modules or blocks such as for the processing of the vehicular processing device(s) described herein.
Figure 8:
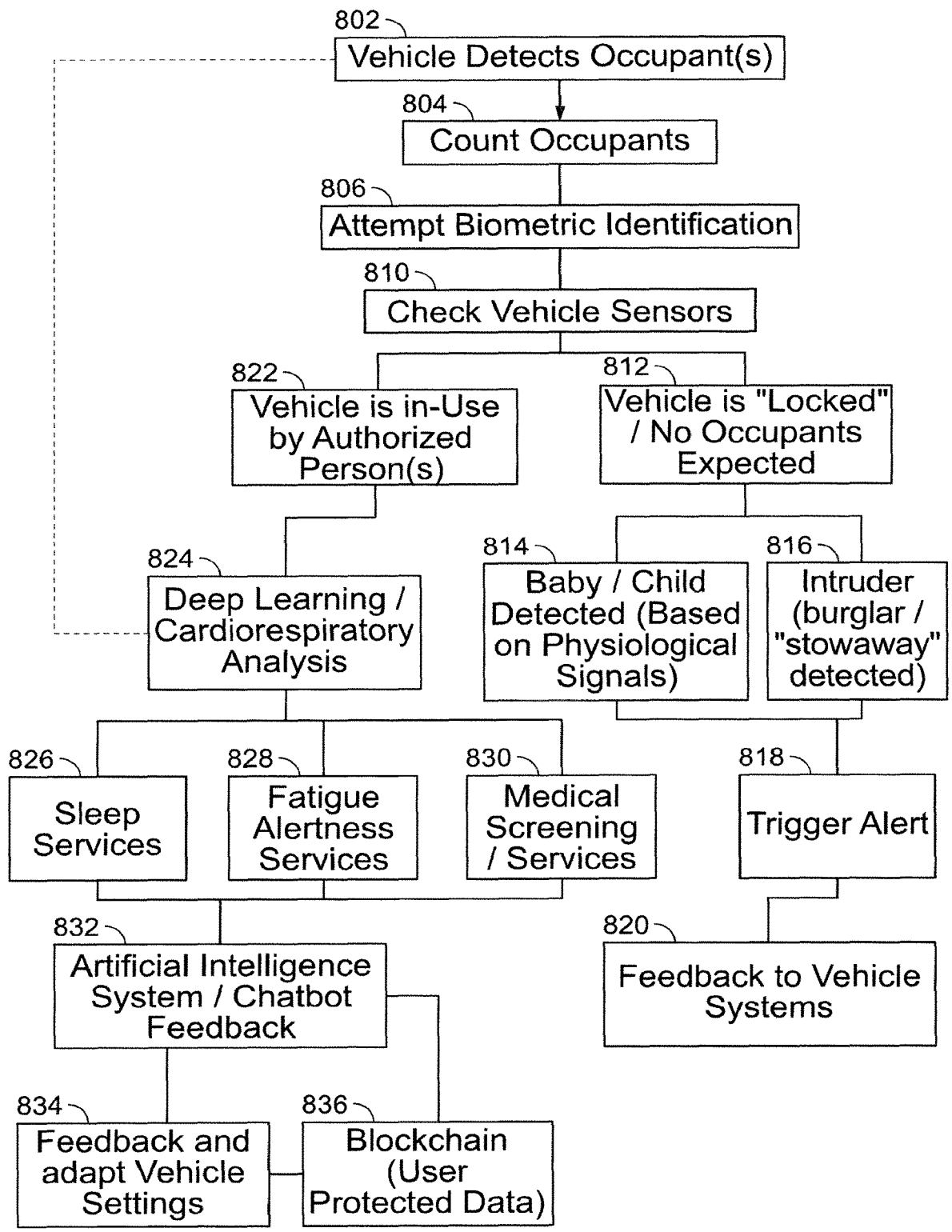
FIG. 8 illustrates example processing flow for in-vehicle motion sensing such as for generating various output (e.g., sleep data, fatigue/alertness data, medical data, a notification data) based on motion characteristics, such as for the sensing device illustrated in FIG. 1.
Figure 8A:
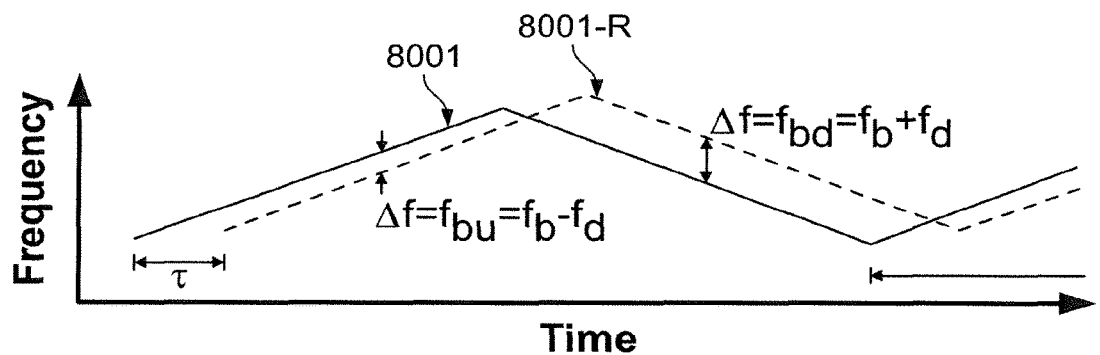
FIGS. 8A, 8B and 8C illustrate various signal characteristics of a triangular single tone such as for a FMCW system of the present technology.
Figure 8B:
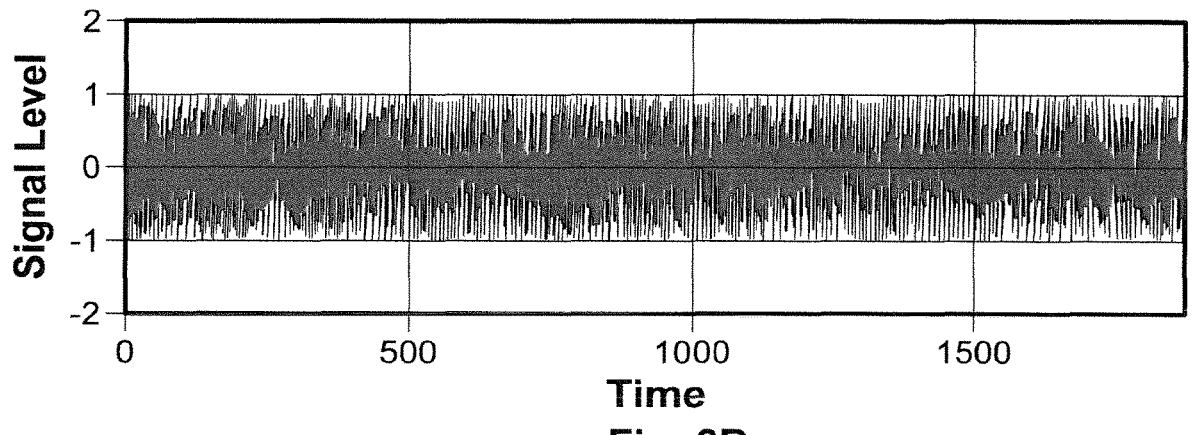
Figure 8C:
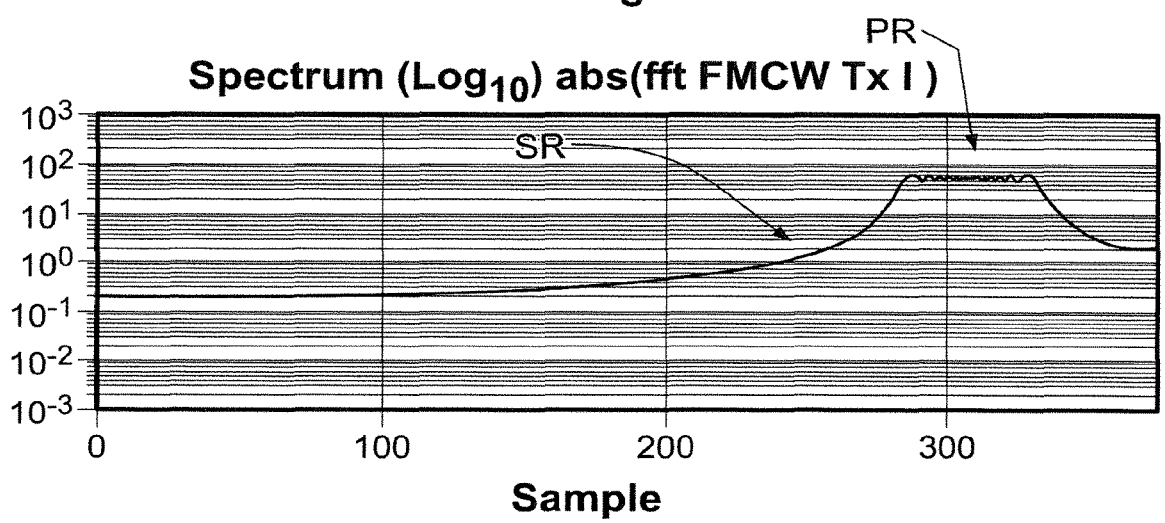
Figure 9:
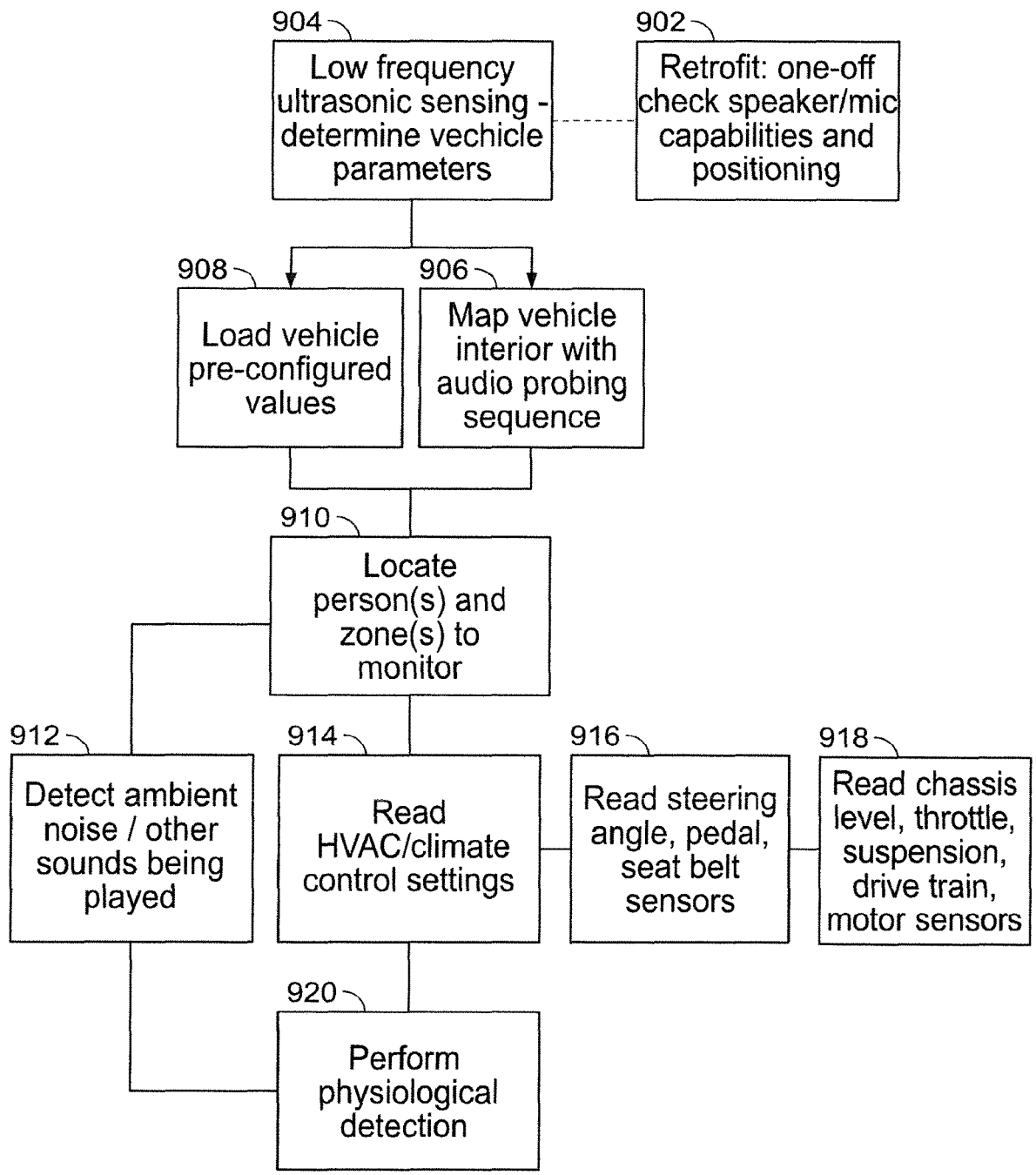
FIG. 9 illustrates example processing flow for an in-vehicle acoustic sensing apparatus, such as a vehicular processing device enabled with SONAR physiological sensing apparatus.
Figure 9A:
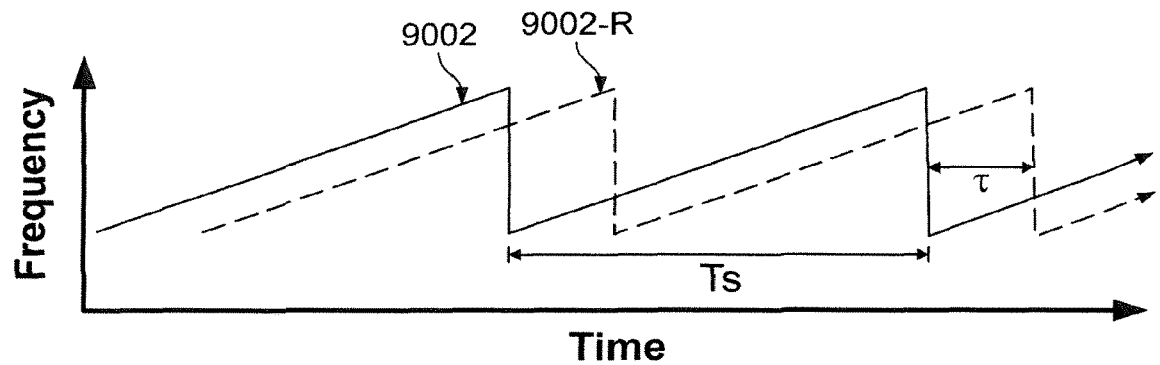
FIGS. 9A, 9B and 9C illustrate various signal characteristics of a triangular dual tone such as for a FMCW system of the present technology.
Figure 9B:
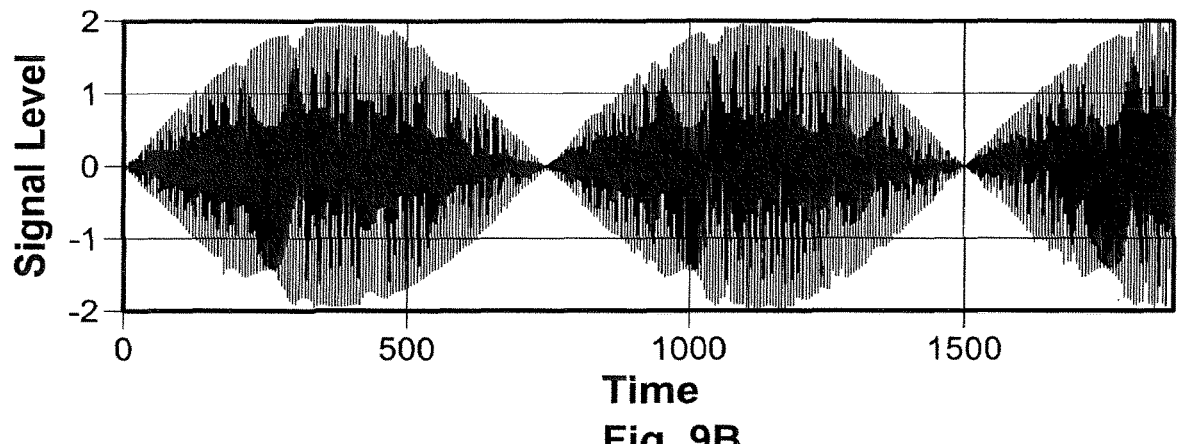
Figure 9C:
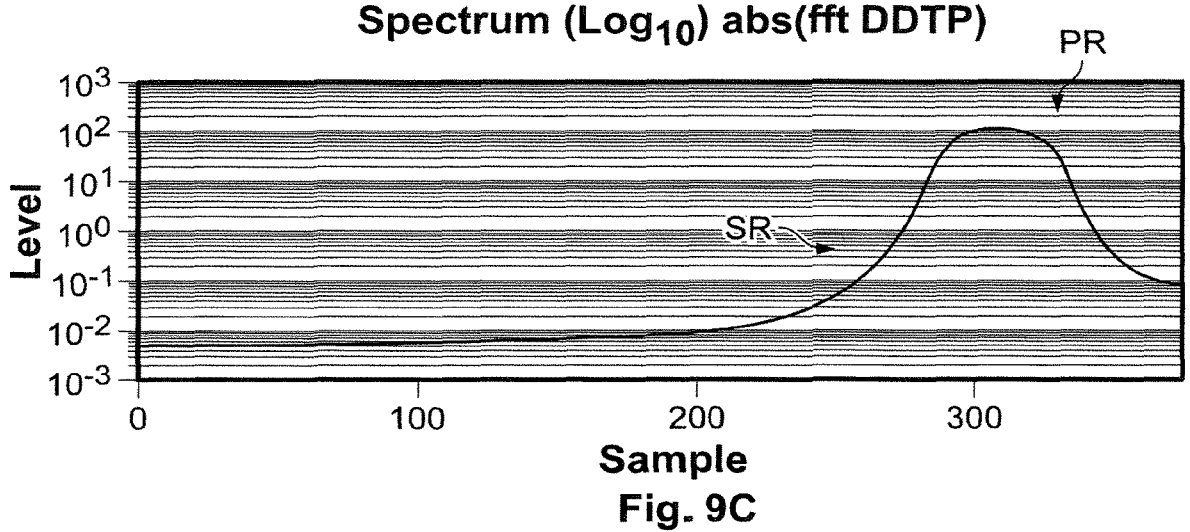

Performance of the FMCW single tone of FIG. 4A and the FMCW dual tone of FIG. 4B may be considered in reference to FIGS. 8 and 9. FIGS. 8A, 8B and 8C show signal characteristics of the FMCW single tone example of FIG. 7A. FIGS. 9A, 9B and 9C show the signal characteristics of the FMCW dual tone example of FIG. 7B.

FIG. 8A shows the transmitted (Tx) signal 8001, and the received (Rx) reflection 8001-R (echo) operating as a triangular single tone FMCW operating in an acoustic sensing system. FIG. 8B shows the time domain waveform. FIG. 8C shows the spectral content of the signal. As evident, there is still content at lower frequencies (outside the peak area relating the bandwidth of the FMCW signal). Such lower frequencies may thus be in an audible frequency range and thereby resulting in an undesirable performance characteristic.

FIG. 9A depicts a dual tone ramp FMCW signal in signal graph 9002. Signal graph 9002 represents both tones, and signal graph 9002-R represents the received echo of the two tones/multi-tone. FIG. 9B shows a cosine-like functional shape of the dual tone, with the zero points (resultant zero crossings). FIG. 9C shows a much smoother peak and lower power amplitude at lower frequencies. The slope region SR of FIG. 9C, when compared to the slope region SR of FIG. 8C, illustrates a sharper decline in power (dB) of the dual tone ramp FMCW in/to the lower frequencies. The sharper roll-off from the range of the high (substantially inaudible, utilised for sensing) frequencies and into the lower (audible, not typically utilised for sensing) frequencies, is a desirable acoustic sensing property as it is less obtrusive for the user. The power at lower frequencies (outside the peak area relating to the bandwidth of the FMCW signal) can be 40 dB less than that in the case of the single tone FMCW triangular form illustrated in FIG. 8C. As illustrated in FIG. 9C, the upper smooth peak region PR of FIG. 9C when compared to the multi-edged peak region PR of FIG. 8C, indicates that the dual tone ramp FMCW signal can have better acoustic sensing properties and is less demanding on the speakers.

Such a multiple tone FMCW or dual tone FMCW system (for example running on a Linux based single board computer) can provide sensing such that it is possible to identify multiple persons within the sensing range of 4 m or more. It can also detect heart rate for example at 1.5 meters from the processing device, and respiration rate(s) at out to approximately 4 meters or more. An exemplar system could use two tones at 18,000 Hz and 18,011.72 Hz, which could ramp to, for example, 19,172 Hz and 19183.72 Hz respectively.

For this ramp of 1,172 Hz, we can consider using, for example, an FFT of size 4096 points, with bin width of 48,000 Hz/4096=11.72. For speed of sound as 340 m/s, we note: 340 ms/s/11.72/2 (for out and back)=14.5 m over 100 bins or 14.5 cm for each bin. Each "bin" can detect up to one person (per bin) for example (but in practice persons would be separated by more than this.) As part of a synchronization process, the signal could be squared, for example, to avoid a more computationally expensive correlation operation, where the signal is multiplied by a reference template. Independent of the FFT size used, the maximum range resolution is speed-of-sound/(Bandwidth*2)=340/(1172*2) =14.5 cm. However, a synchronization process may optionally be provided that includes cross-correlating a sensed reflected signal with a sensed direct path signal. A synchronization process may optionally include multiplying a reference template with at least a portion of the sensed reflected sound signal.

Figure 5:
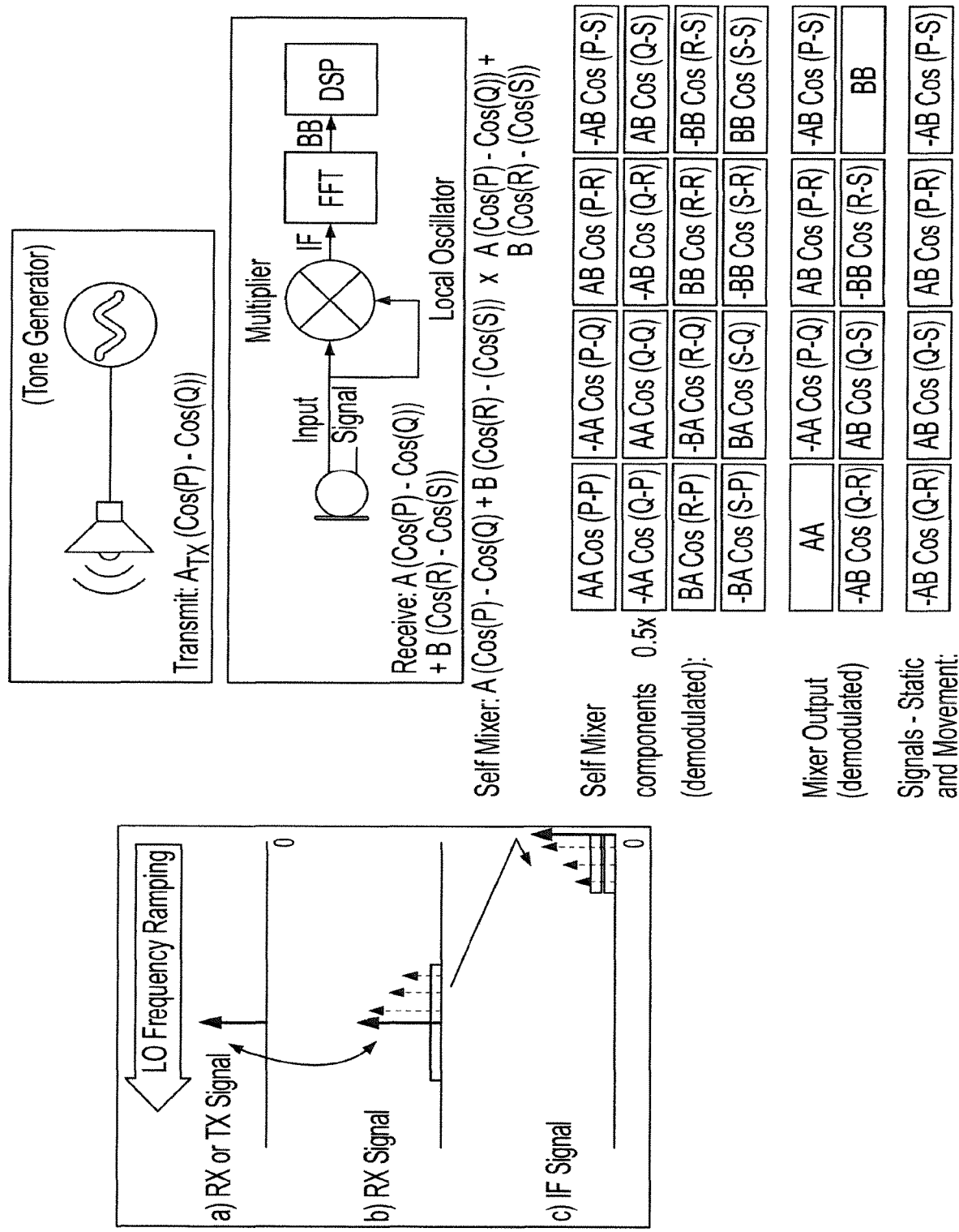
FIG. 5 illustrates example demodulation for a dual tone FMCW that may be implemented for a sensing system in a vehicular processing device of the present technology.

FIG. 5 illustrates an example of "self-mixing" demodulation of a dual tone FMCW ramp by multiplying the signal by itself (squaring). Optionally, demodulation may be carried out by multiplying the received echo signal with a signal representative of the generated transmit signal (e.g., a signal from an oscillator) to produce a signal reflecting distance or motion in the range of the speaker or processing device 100. The processing produces a "beat frequency" signal which is sometimes referred to as an "intermediate" frequency (IF) signal. With FMCW, when the receive Rx signal is demodulated, such as by a local oscillator or by itself as described in more detail herein, and low pass filtered, it may produce an unusual "intermediate" signal that is not yet considered to be baseband. The IF signal may be processed, such as by application of fast Fourier transform processing (FFT), to become baseband (BB).

As illustrated in FIG. 5, the demodulation is conducted with the receive (reflected sound signal) Rx signal only. That is mathematically possible because the Rx signal contains a large percentage of a signal representative of the transmit (Tx) signal (e.g., the produced sound which may, in part, travel a direct path from the speaker to the microphone and be sensed with the reflected sound) in it. The device can multiply the receive signal Rx by itself (such as by just squaring it because demodulation can be considered a multiply operation). This can be followed by a filtering process (e.g. lowpass).

Although FIG. 5 illustrates self-mixing, several different approaches may be implemented to derive a motion signal with the reflected signal, and the sensing signal (i.e., Tx or sound signal). In one such version, a local oscillator LO (which may also produce the sound signal) can effectively produce a copy of the Tx signal for demodulation. The actually produced Tx signal might be slightly different than the internal signal from the oscillator because of delay or distortion. Demodulation can then be conducted by multiplication of the signal from the local oscillator LO(Tx)*Rx which can also be followed by filtering (e.g., lowpass).

In another version, two local oscillators may be implemented to generate two LO signals. For example, a Sin and Cosine copy of the LO signal may be implemented to provide for quadrature demodulation of the receive signal. Typically, only one signal from an oscillator (either Sin or Cosine) is transmitted. The exact Tx signal will be somewhat different from the signal from the local oscillator LO due to delay or distortion. In this version, demodulation may be conducted (a) RX*LO(Sin) and (b) RX*LO(Cos), which may be followed in each case by filtering (e.g., lowpass) to produce both I and Q demodulation components.

Sensing—Mixing (Coexistence) of Acoustic Sensing with Other Audio Playback by the System (Music, Speech, Snoring Etc.)

Some versions of the present technology may be implemented when the processing device 100 may be using its speaker and/or microphone for other purposes, in addition to the ultrasonic sensing described herein. Additional processes may be implemented to permit such simultaneous functioning. For example, the transmit bitstream (acoustic sensing signal) may be digitally mixed with any other audio content (audible) that is being played by the speaker as previously mentioned for simultaneous audio content production and ultrasonic sensing. Several approaches can be used to carry out such audible audio content and ultrasonic processing. One approach requires that the other audio content (which could be mono, stereo or many more channels—such as in many channel surround sound systems) is preprocessed to remove any spectral content that would overlap with the sensing waveform. For example, a music sequence might contain components of over 18 kHz which would overlap with, for example, an 18 to 20 kHz sensing signal. In this case, the music components near 18 kHz can be low pass filtered out. A second option is to adaptively filter the music so as to remove frequency components for the short periods of time during overlapping sensing (direct path and echo), and allow the unfiltered music otherwise; this approach is designed to retain the fidelity of the music. A third option may simply make no changes whatsoever to the music source.

It should be noted that where delays are deliberately added to audio sources on certain channels (e.g., Dolby Pro Logic, Digital, Atmos, DTS etc. or indeed virtualized spatializer functions), any such in-band signals are also accordingly processed, and the sensing waveform will either not be delayed or the delay would be allowed for, when processing the echoes).

Sensing—Coexistence with Voice Assistants

It should be noted that certain realizations of ultrasonic sensing waveforms (e.g., triangular FMCW), may have an unintended and unwanted impact on certain voice assistants that are performing voice recognition services, such as Google Home, as they have spectral content within the audible band. Such potential cross talk can be avoided by using a dual ramp tone pair, or pre-filtering (high pass or band pass filtering the triangular chirp) the sensing waveform, or adapting the voice recognition signal processing to be robust to the ultrasonic sensing signal components.

Consider an FMCW ramp signal y as follows:

$$y=[A \, Cos(2pi(f_1+f_2 t)t+phi]_0^T$$

This ramp from frequency f_1 to frequency f_2 in a time period T. This has sub harmonics as it is switched at a time period of T.

An analysis of this shows that it has out of band harmonics which appear at lower frequencies and so can be heard.

Now consider a specific dual ramp pair y as follows:

$$y=[A \, Cos(2pi(f_1+f_2 t)t+phi]_0^T - [A \, Cos(2pi(f_1+(1/T)+f_2 t)t+phi]_0^T$$

Thus, the sub-harmonics are cancelled (subtracted in the above), and the signal retained. The 1/T is very specific; by using (1/T), or indeed −(1/T), the effect of the switching at time period T is canceled out. Thus, the resulting signal is inaudible. It does this while being mathematically simple, which is an advantage as it is not computationally onerous on a device (e.g., a smart mobile phone device).

Because the dual tone switches at DC level ("0"), there is a natural point in the waveform chirp (a beginning and an end of the signal) to turn off, such as to avoid clicking (i.e., turn on and off in a way to avoid a loudspeaker making a big jump). The "0"'s also allow us to introduce a quiet period between each chirp, or indeed between groups of chirps, in order to mitigate reverberation—and/or to identify a specific transmitter (i.e., to overlay a sequence of on/off chirp times).

The lack of sub-harmonics is also an advantage as it removes a possible source of interference when considering two devices operating in a room at the same time. Thus, two different devices can use non-overlapping (in frequency) tone pairs—or indeed overlapping in frequency (but not in time—due to the addition of non-overlapping quiet periods) tone pairs. The latter can be an advantage where loudspeaker/microphone combinations have limited available inaudible bandwidth (i.e., their sensitivity rolls off severely over 19 or 20 kHz).

Even comparing a relatively inaudible triangular FMCW signal to a dual tone ramp, the latter has a very much smaller level of sub harmonics (approaching the noise floor on a real world smart device—e.g., near the quantization level).

Because a dual tone ramp can be ramped up or down (rather than triangular) and yet have no out of band components, there are no inter ramp bleed problems which can occur with a triangular ramp.

A standard ramp audio signal cannot be made inaudible without extensive filtering, which would potentially distort the phase and amplitude of the resulting waveform.

Sensing—Calibration/Vehicle Mapping to Optimize Performance

The processing device may be configured with a set-up process. When the device is first set up (or periodically during operation) it can send out an acoustic probing sequence to map the vehicle environment, the presence and/or number of people in the vehicle etc. The process can be repeated if the device is subsequently moved, or the quality of the sensed signals is detected to have decreased. The system may also emit acoustic training sequences in order to check the capabilities of the speaker(s) and mic(s), and estimate equalization parameters; real world transducers may have some non-linearities in the ultrasound frequencies used by the system, as well as temperature and turn on characteristics (e.g., as a loud speaker may take several minutes to settle).

Sensing—Beam Forming for Localization

It is possible to implement dedicated beam forming or utilise existing beam forming functionality—i.e., where signal processing is employed to provide directional or spatial selectivity of signals sent to, or received from, an array of sensors. This is typically a "far field" problem where the wavefront is relatively flat for low frequency ultrasound (as opposed to medical imaging, which is "near field"). For a pure CW system, audio waves travel out from the speaker, leading to areas of maxima and minima. However, if multiple transducers are available, it becomes possible to control this radiation pattern to our advantage—an approach known as beam forming. On the receive side, multiple microphones can also be used. This allows the acoustic sensing to be preferentially steered (e.g., steering the emitted sound and/or the received sound waves where there are multiple speakers) in a direction, and swept across a region. For the case of a user in a reclining seat or (travel bed), the sensing can be steered towards the subject—or towards multiple subjects where there are, for example, two persons in neighboring reclining seats (travel beds). Beam steering can be implemented on transmit or receive. As low cost ultrasonic transducers (microphone or speaker) can be quite directional (e.g., for a small transducer, where the wavelength is comparable to the size of the transducer), this can restrict the area in which they can be steered over.

Sensing—Demodulation and Down Conversion

Returning to FIG. 5, the sensed signal is demodulated, such as with the multiplier (mixer) module 7440 shown in FIG. 7 or according to the demodulator of FIG. 5, to produce a baseband signal that may be further processed to detect whether there is "presence" in the sensing field—a disturbance in the demodulated signal that relates to a change in the echoes received, related to a characteristic motion of a person. Where there is a strong received "direct path" (high crosstalk from speaker to microphone, e.g., transmission through a solid versus through air and/or short distance from speaker to mic) signal, in addition to the received echo signal, multiplication of the resulting sum can be performed to demodulate. Otherwise, the received echo can be multiplied (mixed) with a portion of the originally transmit signal, which is extracted in an electronic, and not acoustic, form. In this specific example, the system is not multiplying the receive signal by the transmit signal to demodulate it (although it may other embodiments). Instead, the system may multiply the receive signal (which contains an attenuated version of the transmit signal, as well as the receive echo (es)) by itself as follows:

$$\text{Transmit} = A_{TX}(\cos(P) - \cos(Q))$$

$$\text{Receive} = A(\cos(P) - \cos(Q)) + B(\cos(R) - \cos(S))$$

$$\text{Self mixer} = [A(\cos(P) - \cos(Q)) + B(\cos(R) - \cos(S))] \times [A(\cos(P) - \cos(Q)) + B(\cos(R) - \cos(S))] \text{i.e., receive} \times \text{receive}$$

Self Mixer components (Demodulated) after low pass filtering:

| 0.5× | AA Cos (P-P) | −AA Cos (P-Q) | AB Cos (P-R) | −AB Cos (P-S) |
|---|---|---|---|---|
| | −AA Cos (Q-P) | AA Cos (Q-Q) | −AB Cos (Q-R) | AB Cos (Q-S) |
| | BA Cos (R-P) | −BA Cos (R-Q) | BB Cos (R-R) | −BB Cos (R-S) |
| | −BA Cos (S-P) | BA Cos (S-Q) | −BB Cos (S-R) | BB Cos (S-S) |

Self Mixer Output (Demodulated) after equation simplification:

| AA | −AA Cos (P-Q) | AB Cos (P-R) | −AB Cos (P-S) |
|---|---|---|---|
| −AB Cos (Q-R) | AB Cos (Q-S) | −BB Cos (R-S) | BB | where AA and BB are DC components

Demodulated components that contain reflected signal information (can be static as well as movement related):

| −AB Cos (Q-R) | AB Cos (Q-S) | AB Cos (P-R) | −AB Cos (P-S) |
|---|---|---|---|

The advantages of this are: no synchronization is required between transmit and receive, as all timing information is contained in the receive only, and it is computationally fast and simple (square an array).

After I, Q (in phase and quadrature) demodulation, there is a choice of how to separate the low frequency components relating to air turbulence, multi-path reflections (including fading related to same) and other slow moving (generally non-physiological) information. In some cases, this processing can be called clutter removal. The DC level (mean) can be subtracted, or some other detrending (such as linear trend removal) performed on an overlapping or non-overlapping block basis; a high pass filter can also be applied to remove DC and very low frequency components (VLF). The "removed" information can be processed to estimate the intensity of such DC and VLF data—such as whether there are strong air currents, or significant multipath effects. The filtered demodulated signal can then be passed to a spectral analysis stage. The other choice is not to use high pass filters and to pass the unfiltered signal directly to the spectral analysis processing block, and carry out the DC and VLF estimation at this stage.

Coexistence of Different Sensing Devices/Applications

It can be seen that coded or uncoded ultrasonic signals may be generated by different devices to permit devices and systems to implement identification and other data interchange purposes. For example, a mobile phone application may be configured to generate such signals for communication purposes in order to identify itself to another sensing enabled device/system in its proximity, such as a smart infotainment system of a vehicle and vice versa. These types of signals may be used in place of short range radio frequency communication (e.g., where Bluetooth is not available or is disabled) for identification. The device of the system can then automatically determine existence of other processing devices in the sensing vicinity (e.g., via inaudible acoustically generated communication signals from another processing device) and adjust the parameters of the generated sensing signals so that they can operate in non-interfering sensing modes (e.g., by using different frequency bands and/or not overlapping in time).

Example System Architecture

Figure 6:
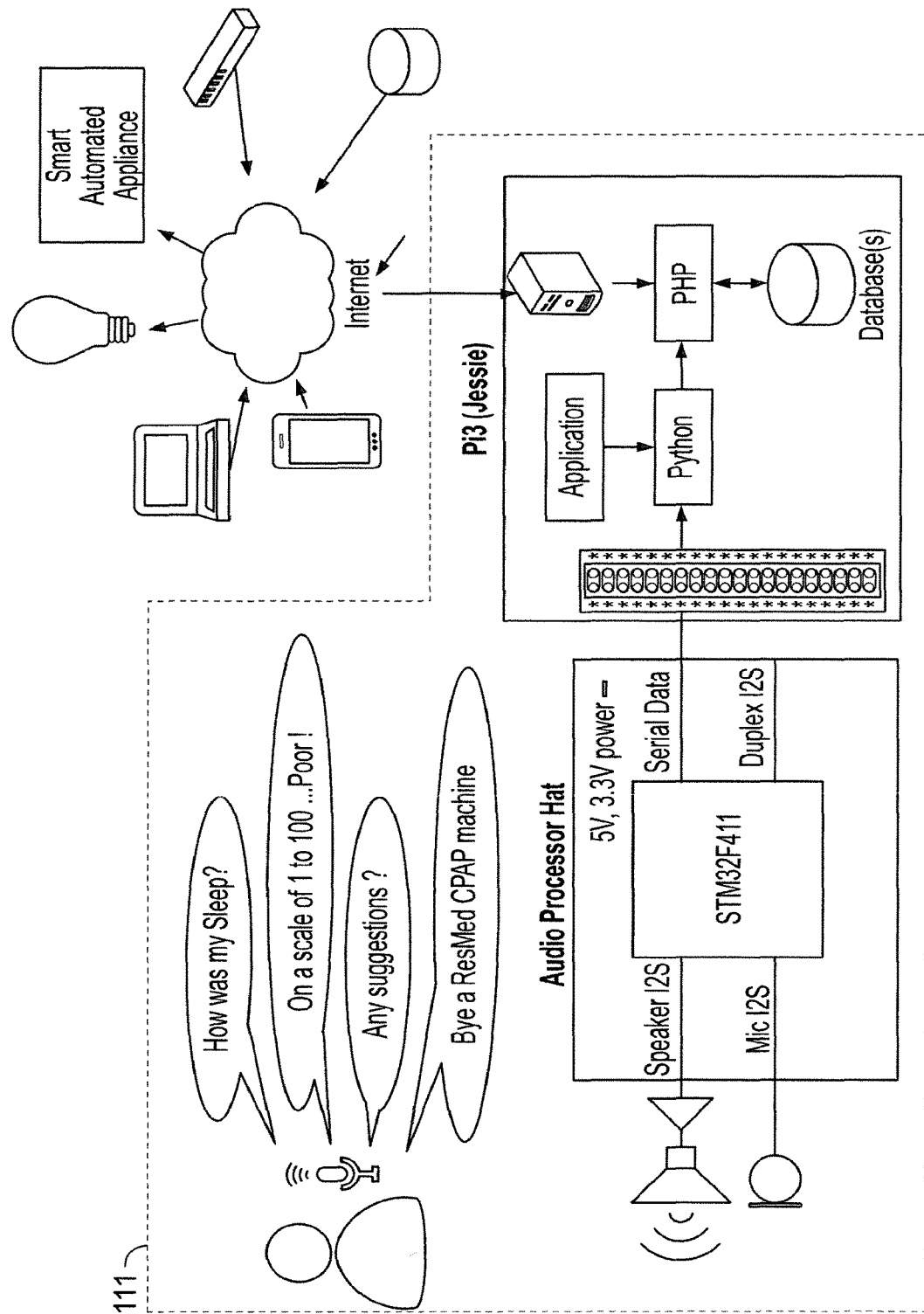
FIG. 6 illustrates example operations of voice enabled audio device or vehicular processing device such as one using low frequency ultrasonic biomotion sensing with signal generation and processing techniques described herein.

Exemplar system architecture of a voice enabled sleep improvement system using low frequency ultrasonic biomotion sensing is illustrated in FIG. 6 in vehicle 111. The system may be implemented with the sensing techniques described herein (e.g., multi-tone FMCW acoustic sensing). A user can talk to a voice activated system such as the vehicular processing device 100 that was previously activated to monitor the user's sleep. For example, a verbal instruction can query the system to monitor the vehicle and produce an audible report of determined sleepiness, sleep score, respiratory (SDB) events, health condition or other motion related statistics. Based on the report, the processing of the system can also produce audible warnings, advice or other control signals for other devices.

System processing for detection of motion in a vicinity of a speaker-enabled processing device 100 that is enabled with the low frequency ultrasonic sensing of the present technology may be considered in relation to the example modules illustrated in FIG. 7. The processing device 7102 includes a speaker(s) 7310 and, optionally, microphone(s) 7302 as well as a microcontroller 7401 with one or more programmable processors. The modules may be programmed into a memory of the microcontroller such as of an in-vehicle audio equipped system. In this regard, an audio sample or audio content may be upsampled by optional upsampling processing module at 7410 and may be provided to a summer module 7420, such as if optional audio content is produced by one or more speaker(s) simultaneously with the sensing signal. In this regard, the summer module 7420 optionally combines the audio content with the FMCW signal in the desired frequency ranges from the FMCW process module 74430 that produces the FMCW signal (e.g., the dual tone FMCW signal in the desired low ultrasonic frequency ranges). The summed FMCW signal may then be processed such as by a converter module for output by the speaker 7310. The FMCW signal is also applied to a demodulator such as a multiplier module 7440 where the FMCW signal is processed (e.g., mixed/multiplied) with the received echo signal observed at the microphones 7302. Prior to such mixing, the received echo signal may be filtered, such as adaptively, as previously mentioned herein to remove undesired frequencies outside the frequency spectrum of interest, such as frequencies associated with the operations of the motor vehicle (e.g., motor vibration or wind sound). An audio output processing module(s) 7444 may optionally down sample the filtered output and/or convert the signal to produce an audio signal. The demodulated signal output from the multiplier module 7440 may then be further processed, such as by post-processing module 7450. For example, it may be processed by frequency processing (e.g., FFT) and digital signal processing to improve the raw motion signal detected or otherwise separate motions by frequency range so as to isolate (a) respiration motion or movement, (b) cardiac motion or movement and (c) gross motion or movement, such as gross body motion or gross body movement, for example. The physiological movement signal(s) may then be recorded or otherwise processed, e.g., digitally, by characteristics processing at 7460 to characterize various motions of the signal so as to detect various informational output as previously mentioned (sleep, sleepiness, fatigue, sleep stage, motion, respiration events, etc.).

In relation to detection of gross movement or gross body motion, such movement may include any of arm movement, head movement, torso movement, limb movement, and/or whole-body movement, etc. Methodologies for such detections from transmitted and reflected signals for motion detection, which may be applied to SONAR sound-type motion detection, may be considered and applied, for example, as described in International Patent Application Nos. PCT/EP2016/058806 and/or PCT/EP2016/080267, the entire disclosures of which are incorporated herein by reference. By the nature of it, such RF or SONAR technology may be seeing all body movement at once, or at least most of it—and it may depend on where exactly the "beam" is directed. For example, is it illuminating primarily the head and chest, or the whole body etc. Leg movement, such as when it is periodic, may primarily distinguished as a motion based on frequency of movement, and optionally by performing different automated gain control (AGC) operations. Respiration detection is most effective when there is less gross body movement, to isolate the characteristic frequencies and signal shape of a breathing waveform (either normal, COPD or CHF changes to rate over time and inspiration/expiration ratio, SDB events, longer term SDB modulation etc.)

When motion is associated with a person in bed, the largest amplitude signals may be associated with a full body movement, such as a roll. A hand or leg movement may be faster (e.g., velocity from I/Q signal) but lower relative amplitude. Thus, different components, and or sequences of components, of such a movement by analysis of a motion signal may be considered in the identification such as whether it starts with gross movement and acceleration, velocity of arm movement, then stops, etc. This identification may be more targeted for different motion gestures.

Low Frequency Ultrasonic (SONAR) Sensing—for In-Vehicle Use

Many vehicles contain audio devices that are capable of emitting and recording sounds in the low frequency ultrasonic range at just above the human hearing threshold—e.g., vehicle infotainment systems. Such devices and systems can be adapted to perform physiological sensing of the vehicle's occupants using low frequency ultrasonic techniques. Such sensing may be performed without impacting the original intended functions of the standard audio systems. In one example, such a sensing functionality can be implemented by way of a software update (i.e., allowing additional useful functionality to be added without increasing the cost of goods). In some cases, one or more of the transducers in a new device or system may be specified to support the audio frequency ranges for low frequency ultrasonic sensing, with additional testing at manufacture to ensure they meet this specification.

Such acoustic (either audible or inaudible) sensing technology can be used for a wide variety of purposes including pro-active health management, medical devices, and security functions.

A low frequency ultrasonic system operating up to around 25 kHz can be realized on a mobile smart device or smart speaker device. This transmits sound energy towards one or more subjects using one or more transducer on the electronic device, where the transducer is configured to generate sound energy over a range of frequencies that includes frequencies less than 25 kHz. The speakers could be contained in a smart phone, a smart speaker, a sound bar, a portable TV screen, or many other devices and configurations that contain transducers capable of supporting low frequency ultrasonic sensing and processing. Many modern vehicles include onboard processors/computers that can control many of the car instruments and functionalities. If such a computer is implemented to control the speaker system of the car or other speakers within the car, it effectively creates a smart speaker system. Whilst aspects of this specification in some instances identifies the vehicle as a car, it is understood that the sensing (e.g., sonar) principals and considerations for a car may be applied to biometric sensing in other types of vehicles, such as trucks, busses, trains, airplanes, boats etc.

Audible sounds such as the sound of breathing, coughing, snoring when asleep, gasping, wheezing, speech, sniffing, sneezing can be extracted and classified from the sensed audio signal within the vehicle so as to permit isolation of these sounds from the reflected sensing signal that will be detected for motion sensing. Some of these sounds (e.g., a cough) can mask the sensing signal (especially if it is operating at a very low sound pressure level), which is not desirable. However, such sounds may still be detectable so that they can be separated from other environmental sounds (e.g., a car horn blowing, motor noise, street sounds, wind, a slamming or closing door etc.). The sound of breathing is typically of better signal quality in a quiet environment, and can provide a good second estimate of inspiration/expiration time (and thus breathing rate) when complimented with an active sensing approach such as SONAR or RADAR (including an RF one) (which are primarily detecting torso and limb movements), or camera/infra-red systems. In other words, the system can still extract information about the characteristics of sounds, even very loud sounds mean that we need to skip small sections of the sensed signal as the associated signal quality drops below an acceptable threshold.

In SONAR systems, the air movement caused by an inspiration or expiration may also be detected by methods that track the resulting travelling wavefront (due to the disturbance of acoustic modes set up in the sensing environment—if the sensing signal persists long enough to experience reverberation). Detecting snoring directly from the audible signature is easier, as it be a relatively loud process for example, by using a running mean filtered maximum decibel level (i.e., max of a filtered section of a signal) to classify snoring as mild (40-50 dB), moderate (>50-60 dB), or severe (>60 dB). (see Nimrod Maimon, Patrick J. Hanly, "Does Snoring Intensity Correlate with the Severity of Obstructive Sleep Apnea?" J Clin Sleep Med. 2010 Oct. 15; 6(5): 475-478.)

Thus, in some cases, the processing device 100 may use motion detection (e.g., Sonar) techniques for detecting respiration. However, in some cases, acoustic analysis, of an audible breath signal at the microphone, may be implemented by the processing device 100 for the detection of respiration.

RF (RADAR) Sensing

Some existing car alarm systems may include single pulse Doppler RADAR modules for simple interior movement detection, especially in soft-top vehicles (convertibles) and/or sports cars. These may be enhanced (with updated software) or replaced with modules that can localize motion detection to specific areas of the vehicle —particularly to be able to detect and distinguish a person on each seat/sitting area. The sensor may be enhanced with technologies such as ultrawideband (UWB) sensing signals or frequency modulated continuous wave (FMCW) sensing signal or including other coding schemes such as OFDM, PSK, FSK etc. in their generated sensing signals. These can be implemented with a sensor having an accurate ranging ability (1 cm or less). Such a sensor may sense in a defined area (e.g., set via the antenna design that may be configured within the vehicle to have a particular seat oriented sensing direction). In some cases, multiple antennas may be implemented for a particular sensing area and may be used with beamforming techniques to set the distance sensing differences associated with the different antennas. Multiple sensors can be used in a vehicle to provide coverage of multiple areas that a person (or pet) could be in (e.g., a sensor for each seat).

Multimodal Data Processing

When using SONAR, RF, or infra-red detectors, a processing device 100 may receive additional data or signals generated by equipment of the vehicle (e.g., to estimate occupancy) so that biomotion sensing may be based on data from such equipment. For example, seat load sensors that detect whether a person sitting on a given seat may provide the biomotion processing device 100 with information to determine when to initiate biomotion sensing with respect to sensing that may be associated with a particular seat. Similarly, seatbelt sensor(s) may detect whether a person has clipped the seatbelt, or whether a child seat is fitted, so as to provide an indication of user presence for user related biomotion sensing. An infra-red system may optionally, for example, be incorporated with a camera system that can track human eye movement, such as for sleepiness detection. Other automobile or vehicle sensors may also be implemented to provide data regarding vehicle characteristics to the processing device for assisting with sensing or generating output. For example, the car's velocity from a speedometer and/or engine revolutions (RPM) from a tachometer may provide the processing device 100 information for filtering sensed signals, such as to remove car related noise (e.g., engine noise or wind noise etc.).

The processing device may be configured with distance information for evaluating relevant ranges/distances for detection of biomotion characteristics. For example, the processing device 100 may have a distance mapping (map) of a vehicle interior—such as of car. Such a map may be provided initially, e.g., at the design stage, to specify an initial sensing configuration. Optionally, the sensing system, under control of the processing device, may dynamically update (or detect) a map of the vehicle (e.g. cabin) when in use by one or more persons. An initial configuration may, for example, capture/detect the position of seats, and most likely seat configurations (such as in in a standard 5 seat car, a minivan, a recreational vehicle etc.); where seats are moveable, sensors can report the current settings to the system to update the sensing parameters (e.g., the position of a person sitting could move with respect to a sensing loudspeaker in a car, as seat slides backwards or forwards, or is folded down etc.).

For the monitoring of the interior of a shipping truck, the location of, for example, pallets of equipment or packages, shelving etc., processing device may include an automatic reconfiguration process with the sensors in order to reject static objects from the analysis, and provide sensing in any free space where a person might hide. For the monitoring of the interior of an ambulance or other patient transportation vehicle, processing device may include an automatic reconfiguration given the moveable nature and location of a stretcher. The interior of a caravan or trailer could also be monitored.

Biometric Feature Detection—Respiration, Cardiac, Movement, and Range

Processing Sensor Signals

The system, including particularly processing device 100, may receive demodulated signals from a sensor (such as from SONAR, RF/RADAR, or infra-red) such as optionally if demodulation is not performed by the processing device. The processing device 100 may then process the signal by separating components of interest such as direct current signals DC and very low frequencies VLFs (e.g., air currents), respiration, heart rate and gross physiological movement signals. These can be estimated/detected by bin searching in fast Fourier transform (FFT) windows, and tracking across windows, and/or via direct peak/trough or zero crossings analysis of a time domain signal at a specified range (e.g., a "time domain" signal for a specified distance range extracted using a complex FFT analysis of the demodulated signal). This is sometimes referred to as "2D" (two dimensional) processing as an FFT is performed of an FFT such as described in International Patent Application PCT/EP2017/073613.

For SONAR sensing, significant other information can be found in the audio band and picked up by the microphone. Such information may be infotainment sounds (music, radio, TV, movies), phone or video calls (including human speech), vehicle noise while in motion or stopped, ambient noise, and other internal and external sounds. Most of these audio components can be considered to be interferers, and may be suppressed (e.g., filtered) from biometric parameter estimation.

For RADAR sensing, signal components from other RF sources such as other vehicles (e.g., for interior biometric detection of people, or ranging functions such as for adaptive cruise control, collision avoidance, autonomous driving etc.) may be suppressed.

For infra-red sensing (such as when carrying out physiological sensing in addition to eye tracking), temperature changes and sun position may cause interference and may be taken into account. Thus, temperature sensors, such as from a vehicle temperature sensor, and time may be evaluated in processing the sensing signal.

Regardless of the exact sensing technique used (RF, IR, SONAR), the received time domain demodulated reflected signal can be further processed (e.g., by bandpass filtering with a bandpass filter, evaluated by an envelope detector, and then by a peak/trough detector). Envelope detection may be performed with a Hilbert transform or by squaring the respiratory data, sending the squared data through a low-pass filter, and calculating the square root of the resulting signal. In some examples, the respiratory data may be normalized and sent through a peak and trough detection (or alternatively a zero crossing) process. The detection process may isolate the inspiration and expiration portions, and in some cases, may be calibrated to detect the user's inspiration and expiration portions.

The respiratory activity is typically in the range 0.1 to 0.7 Hz (6 breaths per minute—such as arising from paced deep breathing to 42 breaths per minute—an atypically fast breathing rate in adults). The cardiac activity is reflected in signals at higher frequencies, and this activity can be accessed by filtering with a bandpass filter with a pass band of a range from 0.7 to 4 Hz (48 beats per minute to 240 beats per minute). Activity due to gross motion is typically in the range 4 Hz to 10 Hz. It should be noted that there can be overlap in these ranges. Strong (clean) breathing traces can give rise to strong harmonics, and these need to be tracked in order to avoid confusing a breathing harmonic with the cardiac signal. At longer distances from the transducer (e.g., several meters), it can be very challenging to detect the relatively small cardiac mechanical signal, and such heart rate estimation is better suited to settings where the user is lying quietly within a meter of the smart speaker—such as on a chair/couch or in bed.

Once absence/presence has been determined as "presence", an estimate of the respiration, cardiac, and motion/activity signals (as well as their relative position and velocity if moving—such as getting in and out of the vehicle) is performed for one or more persons in the field of the sensor. It can be seen that a system that yields ranging information is capable of separating the biometric data of multiple persons—even if the multiple persons have similar resting breathing rates (which is not uncommon in young couples).

Based on these parameters, it is possible to prepare a variety of statistical measures (e.g., average, median, $3^{rd}$ and $4^{th}$ moments, log, square root etc.), wave shape (morphological processing), and then supply to a characterization system, such as a simple classification or logistic regression function, or a more complex machine learning system using neural networks or artificial intelligence system. The purpose of this processing is to gain further insights from the gathered biometric data.

Examples of these insights can be roughly characterized as security related, consumer health related, and medical in nature.

Sleep Staging Analysis

As absence/presence/wake/(NREM) sleep stage 1/sleep stage 2/sleep stage 3 (slow-wave sleep SWS/deep)/REM has a sequence related to the underlying sleep architecture representing sleep cycles, it can be helpful to consider this as a sequenced rather than un-sequenced problem (i.e., reflecting typical sleep cycles, where a person remains in one state for a period of time). The sequence of sleep imposes an explicit order on the observations throughout for example the night (a "sleep").

Some systems may also take advantage of knowledge of a "normal" sleep pattern having a more (higher prevalence) deep sleep (SWS) towards the beginning of the night, and more REM sleep towards the end of the night. This prior knowledge, which could be used to weight (e.g., adjust prior probabilities of these states over time) a classification system for normal sleepers; however, it should be noted that these assumptions from population normative values may not hold for non-normal sleepers, or those that regularly nap during the day—or have poor sleep hygiene (poor sleep habits —such as widely varying 'to-bed' and 'out-of-bed' times).

Classically, sleep staging has been considered in 30 second "epochs" dating back to the Rechtschaffen & Kales guidelines (Rechtschaffen and Kales, 1968) (a manual of standardized terminology, techniques and scoring system for sleep stages of human subjects. U.S. Public Health Service, U.S. Government Printing Office, Washington D.C. 1968) which when looking at electroencephalogram EEG found a 30 second interval ideal for viewing alpha and spindles as a paper speed was 10 mm/s (one page equates to thirty seconds). Of course, the real physiological process of sleep and wakefulness (and absence/presence) will not evenly split into 30 second blocks, so a longer or a shorter time can be selected. The system outlined here preferentially uses a 1 second (1 Hertz) sleep stage output, although it uses longer blocks of data in an overlapping fashion to deliver an update every 1 second (1 Hertz) (with an associated delay related to the size of the underlying processing block). This 1 second output is used in order to better show subtle changes/transitions in the sleep cycle.

Sleep Features—Manually Versus Automatically Generated

The sensed signal (a signal representing distance verses time (motion) information) is used to calculate various features, such as sleep features. These features can then be used to derive information regarding the user's physiological state.

For feature generation, a number of approaches may be implemented. For example, a human expert can manually produce features from the processed or unprocessed signals based on their experience, by looking at the respiratory and other physiological data and its distributions, understanding the physiological basis of particular changes, and trial and error. Alternatively, a machine can "learn" the features with some human supervision (a core concept of the field of "machine learning") where labeled data with the expected outcome is supplied and some human help provided, or in a fully automatic way where some or no labeled data may be supplied.

Deep learning can be broadly considered in the following broad categories: deep neural nets (DNN), convolutional neural nets (CNN), recurrent neural nets (RNN), and other types. Within DNNs, one can consider deep belief networks (DBN), multilayer perceptron (MLP), as well as stacked auto-encoders (SAE).

A Deep Belief Network (DBN) possesses a generative capability, e.g., to automatically generate features from input data. Another approach for this purpose is Fuzzy C-Means clustering (FCM), a form of unsupervised learning that aids finding the inherent structure in pre-processed data.

Handcrafted features can be formed by applying digital signal processing techniques to sensed movement data. A respiration signal in an ideal case is perfectly sinusoidal with two amplitudes (deep or shallow) and a constant frequency (constant breathing rate), described as you breathe in and then out. In the real world, it can be far from sinusoidal—especially as detected from the torso area via and acoustic or radio frequency based sensing approach. For example, an inspiration may be sharper than an expiration, and faster, and there may be a notch on the waveform if breath is held for a moment. The inspiration and expiration amplitudes, as well as the respiration frequency, may vary. Some extraction methods focus on detecting the peak and trough, then detecting the better quality of the two (say detecting a local peak and discarding the trough). This is not ideal if both the peak and the trough times are needed in order to estimate both inspiration and expiration times, as well as volumes (e.g., calculated by integration of the time domain signal versus a calculated reference baseline)—but can be good enough for a respiration rate estimate.

Various methods can be used to assist in the estimate of any of these features, such as the respiratory and/or heart rate or amplitude.

For example, a peak and trough candidate signal extraction requires recovering the respiratory wave shape from noise (and there can be a variety of out-of-band and in-band noise, usually with a preponderance of lower frequency noise which can complicate the accurate detection of lower breathing rates (e.g., 4-8 breaths per minute, which while unusual for spontaneous breathing, can arise if a user is asked to guide their breathing to slower rates). Time domain detection methods include max and min detection after low pass filtering, using an adaptive threshold (that adjusts over a block of multiple breaths to allow deep and shallow breaths to be detected). Optionally, the signal may be low pass filtered and differentiated (e.g., a derivative function). Peaks in the differentiated signal relating to max rate of change may then be detected to provide an indication of breath event. Such a method extracts fiducial points of a respiratory waveform that is modeled as a sinusoid with some noise on it. The LPF removes higher frequency noise. Differentiation is then done and peaks are detected. In effect, this finds points of maximum rate of change of the original signal, rather than the peaks and troughs of the original signal—as a respiratory waveform is often clearest at maximum rate of change rather than a say a wide peak (for example, if there is a breath hold for a short amount of time). A potentially more robust method is to detect zero crossings (around a fixed or adaptive baseline), as the crossings of this boundary is not directly impacted by local changes in the amplitude of the signal.

While respiration signals may be easily visible in the time domain signal (depending on the distance and angle of the chest from the sensor(s)), the cardiac motion is typically a very small signal in comparison to respiration. Higher order harmonics of respiration (e.g., related to the wave shape) can complicate the cardiac signal extraction, and need to be rejected, or detected and excluded.

Frequency domain methods can also be applied, for example to the respiratory data. These methods can include using a detected peak in a band of an FFT (which may be windowed to combat spectral leakage) using a block of data that may be overlapped (e.g., a block of 30 s of data of a data stream that is repeatedly shifted by for example, one second) or non-overlapped (e.g., the data stream is considered to be non-overlapping in thirty second chunks). A power spectral density PSD using Welch's method, or a parametric model (autoregressive) may also be used, with a subsequent peak search. A spectral peak will tend to be wider (more spread) as the respiration signal becomes less sinusoidal, and can include harmonics if the shape has sharp peaks, sharp troughs, or notches. Another method is to use autocorrelation (describing the similarity of a signal to a shifted version of itself), where an assumption is that the underlying respiration wave shape is relatively stable for a period of time, and a periodic local maxima in the autocorrelation can be tracked and filtered by most likely candidate (e.g., not related to noise) maxima in order to estimate breathing rate. Autocorrelation can be carried out in the time domain, or by FFT in the frequency domain. Time frequency approaches, such as wavelets are also useful where a suitable wavelet with a sinusoidal shape are selected (e.g., symlet, Debauchies etc.), that can perform strong de-noising; again, a peak detection is ultimately performed at the time scale of interest (i.e., within the target breathing rate range).

A Kalman filter (a recursive algorithm) can be applied to the time domain signals to estimate the system state; this approach provides a way to predict a future unknown state of a system, based only on the use of the preceding step. In addition to filtering, it can provide signal separation, such as of large movement, respiration, and cardiac movements.

In-Vehicular Sensing (Noise Contaminated Observations (e.g., for In-Vehicular Sensing, but Also Applicable to Detecting Physiological Movement in Other Noisy Environments))

Any detection of respiration peaks and troughs needs to be aware of potentially confounding effects, such as the subject making a large movement (such as rolling in bed or moving while driving), if the subject stops breathing (e.g., an apnea) or exhibits very shallow breathing (e.g., a hypopnea). Using sensing that can track location provides a useful means of separating these effects. For example, a roll can be seen as both a high frequency movement, as well as change in location in space. Therefore, subsequent breaths may be higher or lower in amplitude—but still be "healthy" breaths. In other words, the detected amplitude change may be due to a change in the extracted received respiration signal (after down-conversion etc.) strength, rather than a change in the person's breathing. Therefore, it can be seen that this can allow a novel calibration approach, where the detected distance can be used to relate signal strength to depth of breathing (and hence approximate tidal volume). Where no such movement or displacement is seen, a diminution, cessation, or change (e.g., due to paradoxical movement on chest and abdomen during an obstructive event) of a specified duration range can be identified as abnormal breathing (e.g., an apnea/hypopnea event).

It can be seen that a practical, robust cardiorespiratory estimation system can rely on multiple methods to localize the parameters. For good signal quality cases, a frequency (or time frequency) estimate can localize the likely breathing rate, an estimate of local breathing variability, then extract subtle peak and trough times, and perform calibration with range in order to estimate inspiration and expiration volumes (useful features for sleep staging). Such a signal quality metric is expected to vary over time. If there is a variation in the measured breathing rate, the processing can be done over different time scales, e.g., averaging or median filtering over 30, 60, 90, 120, 150 seconds etc.

In the SONAR case, the envelope of the raw received waveform (e.g., of an acoustic FMCW signal) can be processed as a main, or as a secondary input such as when other additional sensing signals are implemented, for respiration rate estimation (such as for using SONAR to provide extra information for an RF sensing system or vice versa). This is based on the property of detecting the actual disturbance in the air of the exhaled breath of a person. This does imply that there are not other strong air currents in the cabin, room or vehicle (e.g., from an open window, a nearby air conditioning unit, a nearby heater etc.); if there are, their effect on the measurement can either be discarded, or used to detect changes in airflow in the environment.

Large air currents will tend to be detectable as a low frequency movement across range bins (i.e., a perturbation that flows across the range). This is more evident for sensing waveforms that have more reverberation (e.g., that allow the energy of one frequency to build up in the room, and associated room modes).

When considering a sleep staging system that works across a general population (i.e., including users with a normal healthy condition, users with various health conditions, including respiratory conditions such as sleep apnea, COPD, cardiac issues and so forth), it can be seen that the baseline of respiration rate and heart rate can vary widely. Take for example differences in age, gender, and body-mass index (BMI). Women may have a slightly higher baseline breathing rate than men for a similar age and BMI (although a recent study in children ages 4-16 does not show a statistical difference). Those with higher BMIs will tend to breathe faster than the average of somebody of a similar age. Children normally have much higher normal respiratory rate than adults.

Thus, in some versions, the system such as with processing device 100 regardless of sensor type, may be made with a hybrid implementation, such as where initial signal processing and some hand crafted features are formed, prior to applying a deep belief network (DBN). (A hybrid implementation involves a mixture of human "hand crafted," digital signal processing (DSP) derived features combined with features learned by a machine. Initial supervised training is performed using expert score polysomnography (PSG) overnight datasets from a sleep lab or home PSG, from multiple sites around the world, and scored by at least one scorer, using a specified scoring methodology. Further unsupervised training is performed from datasets gathered with one or more of the selecting sensing methods. This allows the system to evolve to reflect new and more diverse data outside of the sleep lab.

In terms of hand-crafted features (i.e., a human engineer/data scientist has designed, chosen or created them), a breathing signal with associated signal quality level is extracted, with specific features of interest being the variability of the breathing rate over different timescales, and the variation in inspiration and expiration time. An estimate of a personalized baseline breathing rate for awake and asleep is formed. It is known for example that short-term changes in breathing rate variability while awake can be related to mood, and changes in mood, whereas these changes while asleep are related to changes in sleep stage. For example, respiration rate variability increases in REM sleep. Longer term changes in breathing rate itself can be related to changes in mental condition, such as providing indicators of mental health. These effects may be more profound when the user is asleep, especially when analyzed over longer timescales, and compared to population normative values.

One can use the variability of the measured respiratory rate as an indication of the user's state (sleep/awake) or sleep stage (REM, N1, then N2, then lowest in SWS sleep). For example, when looking at normalized respiratory rate variability over a period such as 15 mins in a normal healthy person, it is possible to see greatest variability when they are awake; this variability drops in all sleep states, with the next largest being in REM sleep (but still less than wake), then reducing further in N1, then N2, then lowest in SWS sleep. As an aside, air pressure due to breathing can increase in REM sleep, which can have an impact on the acoustic signal detected—a potential extra feature that could be detected in quiet environments or at quieter times.

Such normalized respiratory rate values should not vary significantly between different positions (supine, prone, on side etc.) for a healthy person. However, it should be noted that calibration to the correct tidal volume is likely to be desirable. For example, the system may normalize over the entire night since one person's average breathing rate might be, for example 13.2 breaths per minute (BR/MIN) while asleep whereas another person's average might be 17.5 BR/MIN. Both rates exhibit similar variability per sleep stage. The difference in rate is merely masking the changes that may be considered for classifying the sleep states. The system can consider the average rate (or overall rate graph) for other purposes such as comparing to themselves over time, or indeed to someone in a similar demographic. For a person with obstructive sleep apnea (OSA), it is expected that respiratory variability will increase in the supine position (lying on back)—a potentially useful indication of the user's respiratory health.

Subjects with mixed apnea or central apnea tend to display larger respiratory variability during wake than normal subjects (a useful biomarker), which those with obstructive apnea also have changes versus normal during wake, which are not as obvious (but still present in many cases).

Person specific sleep patterns (e.g., breathing variability) can be learned by the system over time; thus, a system that can perform unsupervised learning, once deployed in the field, is highly desirable.

These patterns can vary overnight (i.e., during a sleeping session) and can be impacted by apneas occurring during the sleeping time, as partial or complete cessation of breathing (or paradoxical movement of the chest and abdomen when there is an obstructed airway). It can be seen that one way to deal with this issue is by suppressing the periods with detected apneas (and the associated oscillations in breathing rate), if calculating sleep stages. One can simply flag apneas and potential micro-arousals, rather than attempting to classify the sleep stage at that point in time. Periodic breathing patterns, such as Cheyne Stokes respiration (CSR), have a strong oscillatory pattern; these may also be detected during a sleep pre-processing stage. While CSR can occur in any stage of sleep, the pauses tend be more regular in Non-REM sleep, and more irregular in REM sleep (information which the system can use to refine sleep staging in subjects with CSR).

Similarly, a cardiac signal can be extracted with processing steps that suppress any harmonics relating to the breathing waveform morphology. Specific patterns such as obstructive, mixed or central apneas are detected, along with any related recovery breaths, and movements related to gasping. From the cardiac signal, a beat to beat "heart rate variability" (HRV) signal is estimated based on physiologically plausible heart rate values. Spectral HRV metrics can be calculated, such as the log power of the mean respiratory frequency, LF/HF (low frequency to high frequency) ratio, log of the normalized HF and so forth.

The HF spectrum of the beat to beat time (HRV waveform) is the power in the range 0.15-0.4 Hz, relating to rhythms of parasympathetic or vagal activity (respiratory sinus arrhythmia—or RSA) of 2.5 to 7 seconds, and is sometimes referred to as the "respiratory band".

The LF band is 0.04-0.15 Hz, which is believed to reflect baroreceptor activity while at rest (and some research suggests may have a relationship with cardiac sympathetic innervation).

The VLF (very low frequency) HRV power is between 0.0033-0.04 Hz (300 to 25 seconds), and reduced values are related to arrhythmias and post-traumatic stress disorder (PTSD).

HRV parameters can also be extracted using time domain methods, such as SDNN (standard deviation of normal inter-beat interval—to capture longer term variability) and RMSSD (root mean square of successive heartbeat interval differences—to capture short term variability). RMSSD can also be used to screen for irregularly irregular beat to beat behavior, such as seen in atrial fibrillation.

In terms of HRV, a shift in the LF/HF ratio as calculated is detectable characteristic of Non-REM sleep, with a shift to "sympathetic" HF dominance during REM sleep (which may be related from sympathetic to parasympathetic balance).

More generally, there is typically increased HRV in REM sleep.

The longer term mean or median of the breathing rate and heart rate signals are important for a specific person when analyzing over time—especially if there is some intervention, such as a medication, treatment, recovery from an illness (either physical or mental), change in fitness level, change in sleep habits over time. They are somewhat less useful for comparing directly from person to person (unless to a very similar grouping). Thus, for breathing and cardiac variability features, it is useful to normalize these (e.g., de-mean, remove the median etc. as appropriate for the metric) such that that can better generalize across a population.

Further analysis of extracted features can make use of a deep belief network (DBN). Such a network is composed of building blocks of Restricted Boltzmann Machines (RBM), Autoencoders, and/or perceptrons. A DBN is particularly useful to learn from these extracted features. DBNs can be used without supervision, and then later trained with labeled data (that is, data confirmed by a human expert input).

Exemplar human crafted "learn by example" extracted features that can be passed onto the DBN, can include: apnea type and location, respiratory rate and variability of same over different timescales, respiration, inspiration and expirations times, depth of inspiration and expiration, cardiac rate and variability of same over different time scales, ballistocardiogram beat shape/morphology movement and activity types such as gross movement, PLM/RLS, signal quality (integrity of measures over time), user information such as age, height, weight, sex, health conditions, occupation etc.). Other statistical parameters such as skewness, kurtosis, entropy of the signals can also be calculated. A DBN will determine several features itself ("learns" them). Sometimes it can be difficult to understand what exactly they represent, but they can often do a better job than humans. A challenge is they can sometimes end up at bad local optima. Once they have "learned" the features, the system can tune them with some labelled data (e.g., data input by a human expert may score a feature (one expert or a consensus of several experts)).

The DBN can also directly learn new features from the input parameters including from the respiratory waveform, activity levels, cardiac waveform, raw audio samples (in the case of SONAR), I/Q biomotion data (in the case of SONAR or RADAR), intensity and color levels (e.g., from infra-red camera data) and so forth.

A machine learning approach that purely uses hand crafted features is a "shallow learning" approach that tends to plateau in terms of a performance level. In contrast, a "deep learning" approach can continue to improve as the size of data increases. The approach discussed above uses deep learning (in this case a DBN) to create new features for classic machine learning (e.g., take new features, a feature selection winnowing by feature performance, whiten with ICA (independent component analysis) or PCA (principal component analysis) (i.e., a dimensionality reduction), and classify using a decision tree based approach such as random forests or support vector machines (SVM)).

A full deep learning approach, as used here, avoids such a feature selection step, which can be seen to be an advantage as it means that the system does not use sight of the huge variety seen in a human population. New features can then be learned from unlabeled data.

One approach for these multimodal signals, is to train a deep belief network on each signal first, and then train on the concatenated data. The rationale for this is that certain data-streams may simply not be valid for periods of time (e.g., the cardiac signal quality is below a usable threshold, but there is a good quality respiratory, movement, and audio features signal available—in which case, any learned or derived features from the cardiac data would be nonsensical for this period).

For classification, a sequence based approach such as Hidden Markov Models (HMM) can be applied. Such a HMM can still optionally be used at the output in order to separate the sleep stages, in order to map an output sleep graph to a stepped "sleep architecture" as might be provided via a hospital sleep lab PSG system, and minimize unusual sleep stage switching. However, if we recognize that sleep is a gradual physiological process, we may prefer to not force the system to a small number of sleep stages, and allow it to capture gradual changes (i.e., to have many more "in between" sleep states).

A simpler state machine approach with no hidden layers is possible, but ultimately can have problems generalizing across a large population of sleepers, each having their own unique human physiological characteristics and behaviors. Other approaches as Conditional Random Fields (CRF) or variants such as Hidden State CRF, Latent Dynamic CRF, or Conditional Neural Fields (CNF) or Latent Dynamic CNF. It should be noted that Long Short-Term Memory (LSTM) can have good discriminative ability, particularly when applied to sequence pattern recognition (more typical in normal healthy sleepers).

Semi-supervised learning could be performed using a recurrent neural network (RNN), which can be effective in finding structure in unlabeled data. An RNN is standard neural net structure, with Input, Hidden Layers, and Output. It has sequenced input/output (i.e., the next input depends on the previous output—i.e., hidden units have recurrent connections that pass on information) using graph unrolling and parameter sharing techniques. LSTM RNNs are well known for natural language processing applications (with LSTM to combat exploding and vanishing gradient problems).

In terms of detecting sleep onset, if a speech recognition service is running, voice commands by the user can be used as a second determinant of "wake" (not to be confused with nonsensical sleep talking). If a personal smart device is used (unlocked by the user—then with UI input, movement of the accelerometer, gyroscope etc.), this can also be used as a determinant of wake to augment other sleep/wake sensing services.

Automotive Sensing (Related to Self-Propelled Vehicles or Machines):

Low frequency ultrasonic sensing can also be used in an automotive/vehicular setting (e.g., in cars, trucks and other transport types). In-car entertainment (ICE), or in-vehicle infotainment (IVI), is a collection of hardware and software in automobiles that provides audio or video entertainment. The availability of associated speakers, microphones and processing electronics can be used for SONAR sensing.

There are several different types of applications.

For example, the technology can be implemented for security applications such as to detect occupancy of a vehicle, such as for a child or baby accidentally left in a vehicle, stowaways in the back of a truck, driver taking a nap in a truck, or an intruder that has broken in to a vehicle. Thus, when a user leaves a vehicle the processing device may generate an alarm if a person is detected by motion sensing within the vehicle, such as upon sensing a door closure with a door sensor and sensing that the vehicle is turned off with a motor operations sensor. The sensing techniques of the processing device 100 may also be configured to detect a person in a vehicle at an unauthorized time in a traditional intruder alarm situation and generate an alarm.

The technology of the processing device may also be implemented to monitor breathing, cardiac signals and motion when a vehicle is stopped or in motion to check health state, monitor fatigue, alertness, or sleep state (asleep or awake) and/or sleep stages (light, deep, REM, stages 1 to 3 etc.).

For vehicles with systems such as lane departure, seat sensor, and/or eye tracking, the technology can provide extra information about the attention level of the driver. For example, the processing device may detect sleepiness by evaluation of sensed motion (e.g., respiratory, cardiac and/or gross body motion) and generate an alarm upon detection of sleepiness.

For semi-autonomous vehicles, the processing device 100 can evaluate signals/data from other sensors such as steering wheel pressure or user grip (e.g., strain gauge, touch sensors or force sensors) and steering wheel angle (e.g., optical sensors) in order to ensure that the driver's alertness level and health condition are such that the person remains attentive for intervening if the driving system encounters an unusual or dangerous situation which would otherwise benefit from a human involvement (e.g., requiring an ethical decision to be made).

For fully autonomous vehicles where user (driver) intervention is not required, the processing device 100 can be used to, as described above, so as to monitor user sleep and provide customized sleep programs to allow the occupant(s) to get a good sleep or nap so that the user can wake up, alert and refreshed at their destination. Optionally, the processing device can monitor the user's health condition and in the event of detection of a dangerous condition of a user/passenger (e.g., heart or respiratory failure) the processing device may generate a communication with an alert (e.g., to a medical destination) and/or change a navigation route of the vehicle to the medical destination (e.g., nearest hospital) and set/control movement of the vehicle with an autonomous control system to drive to the medical destination. Optionally, in response to such a detection, a semi-autonomous or autonomous control system may control the vehicle to come to a safe stop and generate a communication (e.g., an automated voice mobile telephone call) identifying location of the vehicle to emergency medical support and identifying the nature of the emergency.

The technology can be implemented: 1/ in existing vehicles with speaker/mics and vehicle control systems that can be upgraded (e.g., by updating the system's software), 2/ in new vehicles infotainment designs, add-on/aftermarket systems can be installed to enable the sensing and associated services, and 3/ in any vehicle, portable systems such as smart phones or smart speakers can be activated and used for the sensing and user interface.

Support Existing Fleet of Regular Vehicles—Security and Protection

For example, the sensing capabilities can be implemented in a car using an existing stereo system (for example where separate tweeters (loudspeakers designed to reproduce high frequencies)) are included, although simple single cone full range speakers can also be effective) to detect absence and presence. Preferentially, this sensing capability would operate when the car is running, but it could also be employed at very low power levels when the vehicle is parked to detect a person or animal breathing for safety reasons (e.g., to detect and raise an alert if a child or baby or indeed a pet was left in the car accidentally). An advantage of such a system is that it does not require changing of existing car hardware. For example, the sensing capability can be implemented as a software upgrade to a head-unit/amplifier (especially where the head-unit supports applications). Thus, existing car fleets can be upgraded at relatively low cost. In many such cases, such systems include one or more microphones having noise cancellation features and are of sufficient quality to serve as sensors as described herein. In this regard, they have a frequency response capable of sensing the audio signals described herein (e.g., low ultrasonic frequencies).

Add-on Kits/Smartphones

Aftermarket Bluetooth car kits (either wired in to the car speakers or standalone) may also be upgraded to include the sensing technologies describe herein.

Furthermore, if a smartphone is used in the car, the smart phone could operate as a processing device including an application that provides a configuration for in-vehicle sensing.

Speaker and Mic Locations for Sensing

Careful selection of speaker and microphone location is beneficial for achieving accurate sensing of the driver, such as where hand movements related to steering wheel, gear change, and leg movements are expected. Use of dash locations near the A-pillar and door card or door panel (which are actually quite common in multi speaker systems) can provide a good view of the chest. As a result, typically, passengers will have less "motion" than the driver.

If more speakers than microphones are available, the processing device 100 may operate different individual speakers to monitor different individuals, while sensing with a common microphone. For example, the processing device may generate sensing signals at different sensing frequency ranges for different speakers. If possible, separate microphones may be configured in the front and rear of the car to provide some spatial separation. Ideally, a speaker and microphone combination may be implemented for each seat location (i.e., for each person), as part of the overall in car entertainment system.

There are a variety of different sensing scenarios (which can benefit from different sensing waveforms/schemes) such as the scenario to detect one or more specific person(s) in a car (e.g., individual sensing for each seat) versus detecting anything in car (which may be more useful as an occupancy detector for security/safety purposes) versus detecting anything in a larger space (e.g., a large truck, shipping container etc.).

One challenge relates to differences in noise level with engine noise (internal combustion engine), hybrid and electric powertrain cars. There may be engine/motor noise, mount transfer, body transfer, and resulting interior noise from same. Other than powertrain induced noise, there are differences in tire noise ratings (as well as wear levels), rattling of the car body, size and shape of the cabin (e.g., dead space and echoes), wind induced and road induced noise. A car is a difficult place to critically listen to a sound system because of noise and the cabin configuration. Reflections, standing waves, resonations, uneven interior surfaces, resonant frequencies, and less-than-adequate space for proper speaker placement can affect sound quality.

In terms of directionality of speakers, sensing can be affected by where a speaker is pointed at a person (e.g., if placed in the door card) or whether it requires multipath detection (e.g., a dashboard speaker reflecting from the windscreen, a rear speaker facing upwards in the rear parcel shelf).

There is scope for significant reverberation in car (as it could crudely be considered as basically an enclosure), but there can be a benefit in that the user is generally in a relatively static location.

Cars are typically designed as a means of transportation first, and as a listening environment much later (potentially one of the much later design steps). This may change over time as infotainment systems are improved.

Ray tracing is a predominant means of modelling car acoustics at >4 kHz. This is applicable for a new car design, but may not be feasible for a retrofit system, where the system seeks to quickly model/map the interior of the car (e.g., with an audible or inaudible probing sequence). Changes in furnishings, seat types, dashboard reflections, differences in windows down (partially or completely) affect sound differences from one vehicle to the next. There can be significant differences between an SUV and other types of cars (e.g., a cabrio/soft top/targa configuration).

The most straightforward vehicle configuration has tweeters (speaker) pointed towards the front seats (which is a common setup used by car manufacturers). In this case, there may be a specified distance from speaker to midpoint of a seat, and the system can model the depth of a person sitting on the seat. The system can detect the side and front of the person for the case of a speaker mounted high up in the door (a typical location for a tweeter) or on the side of the dash or A-pillar. Thus, the frequency range and modulation scheme may be tailored to the likely distance by the system. The system can also select a scheme that is robust to reverberation noise (i.e., that does not allow the sensing energy at any one frequency to build up in the car). One such example is a scheme employing dual ramped FMCW. Such sensing may be turned on and off by the system between each cosine-like sequence, and also the system may adjust the ramped frequencies between each sequence (taking advantage of the "zero" points to avoid audible clicking of the speaker). Such system adjusting of frequencies is desirable in an automotive setting, due to the variable nature of in-cabin noise. For example, an internal combustion engine based sports car with a sports exhaust system and significant induction noise is very different to an electric car, although the electric power train can have whine at higher frequencies.

Where premium audio systems are installed, or aftermarket systems, the tweeters can be rated to over 30 kHz, which provides a wide operating band (assuming that the amplifier components are using an adequate sampling rate to avoid aliasing). Depending on the tweeter manufacturer, an upper range of 21-30 kHz may be available. A system may use slightly higher or lower frequencies depending on manufacturing variance of specific parts. Availability of such frequencies may be detected by a setup process (i.e., to determine the capabilities of the parts installed).

Microphones are often placed in the headliner for active audio cancellation or hands-free phone use. These are in a useful position to detect the reflected signals from the front passengers. Proposed audio cancellation systems typically have speakers mounted midway up the door, and multiple microphones (e.g., at least 4 mics in the vehicle). This type of configuration is suitable for biometric detection and biometric identification/recognition. Microphone frequency response will ultimately limit the highest usable frequency (e.g., a mic rolling off at 20 kHz with tweeters capable of 25 kHz will ultimately limit the system to 20 kHz). Availability of such frequencies may be detected by a setup process (i.e., to determine the capabilities of the parts installed).

Other configurations may be implemented without standalone tweeters, where there are larger cone speakers lower down in the doors that can still produce above 18 kHz. This means that lower frequency ranges should be used.

There may be only one microphone placed near the driver. In this case, the system can still function, as different frequency bands and/or coding schemes (e.g., re-using frequencies ranges, but separated in time) can be used. So four passengers could utilize four speakers where each speaker monitors one person. This may be implemented, with ideally four microphones. However, it could be implemented with one microphone, where the processing device select different range bins in an FMCW system (i.e., use the estimated time for the sounds to reach the torso of the respective passenger) for the different passengers.

Heating, Air Conditioning, and Windows

The processing device 100 may be configured with the vehicle sensing system so that it can detect whether the car windows are open versus closed, such as by accessing a signal from a window sensor. In some versions, the processing device may be configured to communicate with a CANBUS system of the vehicle (where available) to receive signals from any of the sensors of the vehicle. For example, to automatically adjust (or query the current position of) electric windows, a message can be generated by the processing device on the vehicle network that is communicating with the appropriate door module (e.g., a passenger door module). Some of these implementations are vehicle manufacturer system specific (i.e., not part of the OBD protocol), and can use data from an existing position sensor.

For example, different parameters of air conditioning/fan settings (e.g., detecting which vents/flaps are open (direction of airflow), fan speed etc.) on air blower system can also be read from the vehicle control systems by the processing device, and serve as a basis for making adjustments to the sensing signal (e.g., changing its amplitude and/or waveform(s)) to facilitate suitable physiological parameter signal quality recovery with the sensing signal. Such adjustment could include adaptively changing the frequency band that is applied for sensing to one that is suffering less interference, and/or to change the sensing waveform to have more or less reverberation. Other parameters such as detecting if the car/vehicle doors open or closed, or steering wheel hand removal etc. can also be obtained by the car sensors.

Autonomous Vehicles—Sleep, Fatigue and Alertness Sensing

Artificial intelligence systems for autonomous driving are on the rise. Depending on the autonomy level of the autonomous vehicle, the desire may be to promote sleep on the move or stopped, or to detect fatigue/sleepiness prior to sleep to make an intervention.

In fully autonomous vehicles, a steering wheel, pedals and other controls might not be included. This provides new opportunities in terms of re-using the vehicle compartment space as sleeping quarters or a work area (or even for exercise) during travel/commuting.

The persons in the vehicle can have their vital signs monitored both while awake and asleep using, for example, the low frequency ultrasonic sensing.

When they are asleep, the processing device 100 can have their respiratory waveforms checked in order to screen for sleep apnea, and breathing and cardiac rates checked for signs of illness. The processing device 100 can then present a sleep score, as well as a fatigue score. The system offers the opportunity to manage insomnia, and other sleep conditions.

Breathing entrainment exercises can be provided to help induce sleep in such an autonomous vehicle. The whole environment of the vehicle can automatically adjust to promote good quality sleep. For example, the processing device 100 serving as an infotainment system can be configured to produce active noise cancellation to reduce vehicle noise. In some cases, the processing device might control light within the vehicle. For example, it might make a controlled adjustment to window transparency to reduce light or raise light for wake time such as with controllable glass or electrochromic glass to darken or lighten). It may control automatic blinds on the windows for light adjustments and/or other devices to set acoustic treatments or sound barrier (e.g., sound absorbing window covers) in positions to make a quiet environment in the vehicle.

When they are coming close to the destination, the processing device of the system, can consider, for example, the GPS vehicle location from a GPS sensor of the system, time of sleep or travel, and/or the detected sleep state of the users, can control these devices to increase light and sound levels in order to gently wake the user.

As a passenger in a "robo-taxi" or ride sharing vehicle, the processing device can include a relax and sleep program to induce either with sound and/or visualizations controlled and produced by the processing device. Optionally, the processing device may also be configured to evaluate respiration during sleep such as to carry out a sleep apnea test on the move (e.g., counting arousals, apneas, hypopneas) and reporting them to the user on waking.

Notably, the above applications/operations may also be implemented in systems (e.g., entertainment systems) included within standard driver-operated busses and trains currently providing transportation on roads and railways. These vehicles are often used by passengers for long days and/or overnight trips. These operations may also be implemented in entertainment systems of airplanes.

In a semi-autonomous vehicle, the detection of wake (rather than sleep or pre-sleep) is important to ensure the driver can react to any unanticipated road situation as part of the human-to-machine interface. For example, depending on the level of autonomy of the autonomous vehicle, a processing device of such a vehicle may require the user to be able to intervene—i.e., they must be alert and "present". Such a system could be integrated to communicate with other car drowsiness aids, such as sensors in seats, cameras performing eye tracking etc. The system may implement a voice assistant to talk to the driver to judge their current alertness level based on the responses, and take action if they are likely to enter micro-sleep. For example, such a car may increase sound as an alert and/or pull the car off of the road and stop to allow the driver to sleep or wake up. Thus, motion detection capabilities such as the sleep or wake detection operations of the processing device 100 may serve as an input to vehicle control operations so as to control an adjustment of a vehicle operation (e.g., movement of the vehicle, reduce speed, stop, pull over, and/or change destination or offer a navigation destination to a location to help driver (e.g., coffee shop or hotel)) based on the detection of wake or sleep.

In some cases, based on such detections, the system may control operations to discourage sleep. For example, it may generate a sound, such as a distracting sound. Such sound may help for a short time before the person falls asleep—but may be enough to allow them to drive somewhere safe to stop for a coffee or nap—or to activate a full autonomous return-to-home navigation and/or autonomous driving function. In example, a distracting sound might include starting with a default cabin chime or other vehicle error sound. Such a sound may then include spoken commands to wake up. Operations may include shaking the driving wheel (such as with integrated vibrator(s)) or even the car seat back (such as with integrated vibrator(s)) by control of a mechanical shaking device.

User Personalization within and Between Vehicles

There is a move from car ownership to a "mobility as a service" business model. This implies that users no longer need to own a car. Longer lasting cars also promote such a service (i.e., move from internal combustion engines to electric motors) as well as urban/city living, and improvements in car and ride sharing services. It may also be promoted by requirements of city authorities to reduce congestion and increase air quality.

Processing devices of such vehicles can be configured to allow transient personalization of the vehicle with user-customizable parameters. This allows personalizing the user experience across many vehicles—whether it is in a car that is regularly re-owned, a car sharing service, or a ride sharing/public service vehicle. Such parameters can include a customized and personalized sleep/nap configuration—which is particularly relevant where there is a separate human driver, or an autonomous vehicle.

For example, the processing device 100 of the vehicle may monitor the user's sleep in challenging automotive environment—including for example noise, motion, fans/airflow. In order to promote sleep, the processing device may be configured to select and optimize a navigation route, adjust suspension settings and/or automated vehicle control style (e.g., driving casual rather than aggressive such as by adjustments to acceleration and/or braking) to enhance the user's sleep. Subject to user's instruction or it current operational mode, the processing device 100 of the vehicle may even select a longer route to a destination to allow sufficient time for a nap (in order that the user(s) gets part or all of a sleep cycle in order to wake up refreshed/minimize sleep inertia), and/or for comfort (select a route with better road surfaces, fewer predicted braking/acceleration or cornering events, etc.).

The processing device 100 may control a light adjustment and window coverage adjustment so that the vehicle changes the interior lighting (both intensity and hue). The processing device 100 of the vehicle may then play music and/or apply active noise cancellation or masking sounds (e.g., white noise) such that the environment is optimized for relaxation and sleep. For a vehicle with seats that can adjust or a bed, in the relax phase, the processing device 100 may control a massage based on controlling motors and actuators in the seats. The processing device 100 may then mute non-safety-critical notifications during the sleep or nap time. For a longer trip, the system can offer any one or more of the following programs: relax, sleep, waking, work program. The processing device 100 may control a switch to work, relax, sleep, waking, work programs to suit (or be more aligned to) the circadian rhythm of the user. For example, the processing device might offer a nap (or delayed a requested one) to correspond to an afternoon "dip" of a user, where the user is on a long journey.

Pre-Sleep in Moving or Stationary Vehicles

For people prone to motion sickness, a nap or sleep time with an initial relax phase using deep breathing (with optional audio cues or synchronized music provided by the processing device 100 to guide the user to achieve deep breathing) with eyes closed, can help reduce any such sickness. The vehicle suspension may be controlled by the processing device to perform more correcting actions in order to reduce the feeling of motion sickness, and may move a sleeping position (e.g., a controllably adjustable seat) towards the front of the vehicle if many corners and bumps or grade changes are expected on the route.

The processing device 100 could start a guided breathing exercise with monitoring the user's breathing rate to estimate an initial baseline respiration rate, and baseline inspiration time to expiration time ratio, along with depth of breathing (e.g., shallow inspiration and expiration). It can then provide an audible or visual (but audible is preferred if the user is relaxing and intending to sleep) cue for the person to adapt to inhale for a count of four seconds, and then exhale for a count of four seconds, all through the nostrils (i.e., mouth closed). If the user can sustain this for 10 or more breaths, they may be allowed a short recovery time, then guided to slower breathing (moving from 4 to 6 to 8 seconds for inhalation, and the same for exhalation) in order to determine what is comfortable, achievable, and sustainable (based on monitoring the actual respiration waveform). A guideline time is 5 to 15 minutes for this exercise. In terms of positioning in the vehicle, this depends on whether the breathing program is for relaxation, or sleep—and the adjustment of the seat/bed.

Optionally, the processing device may generate control signals to control a seat that include motors/actuators so that the seat acts as a massage seat.

This can be extended to an abdominal (diaphragm) breathing exercise. If the person is in a seat that is relatively upright, they may be asked to place one hand on their chest, and another hand on their lower stomach. They are prompted to breathe deeply via their nostrils such that their lower hand moves, but not upper hand (as much as possible). Gesture recognition sensing can be performed by the processing device 100 using its sensing operations to confirm that the lower arm is moving more than the upper arm. Heart rate and detection can be performed to confirm that the exercise is having the desired effect (reducing heart rate, and increasing heart rate variability to their personal baseline "relaxed" ranges).

As the user falls asleep, the seat can be controlled by the processing device to adjust it to provide suitable support.

For longer journeys, the system can adjust navigation parameters to add comfort breaks to the sleep/nap program, to bring the user to a safe place with a restroom and/or an area for a walk. This might be coordinated with a battery or fuel recharge, or battery swap event.

Sleep Disordered Breathing (SDB) Screening

Where non-contact sensing is deployed by a processing device in a public service or ride sharing vehicle, the passenger(s)/user(s) (i.e., single or multiple occupancy) can be asked by a voice assistant of the device if they wish to opt in to physiological monitoring. If they choose to do so, while awake, the system can monitor their cardiac and respiratory parameters automatically. If they sleep with one or more sleep cycles, the system can monitor their sleep stages, as well as check for apnea or hypopnea events. Such a system can be implemented in any vehicle such as a non-autonomous car where there is a driver, in an autonomous car as part of a car sharing service or taxi service, or a vehicle with a berth/sleeping area (truck, train, plane, etc.).

System for Alertness

Non-contact sensing of alertness can be used to augment safety systems in vehicles where the user may be requested to make a safety decision—such as overriding an autonomous vehicle, or as part of a lane departure detection or drowsiness detection system. Such sleepiness or fatigue detections may be made using any of the methodologies described in International Patent Application No. PCT/AU2014/059311.

Security Applications

Illegal immigration can be an issue for customs and immigration as well as prison authorities, police, and freight operators.

It can be seen that non-contact sensing by a vehicular processing device 100 may be configured to detect the presence of a respiratory signal in a monitored space (such as when the vehicle is parked) and alert the driver and/or a central monitoring service. The system may be configured to detect masking and/or interfering signals that affect the sensing signal so that changes may be made to the sensing signal to avoid the interference. Thus, the processing device of the system may correctly detect a respiratory signal, or otherwise report a sensing fault if interference is detected. The system can benefit from the fact of multipath modal behavior to perform biometric identification of a person, with detection of unique biometric signatures. Such signatures can be influenced by the cabin (e.g., the system can select sensing signals that cause reverberation in the sensing space —akin to detecting ripples on the surface of a swimming pool).

Protect Vehicle

Vital signs monitoring in the vehicle can be used to confirm an intrusion into the vehicle, and work with other intrusion sensors (e.g., door contact switches and car alarm systems).

Protect Persons (Children or Babies) or Pets Left Unattended in Vehicle

As previously described, by detecting respiration and heart rate in a recently vacated or intended vacant vehicle, alerts can be generated by the processing device if a child or baby or pet is left accidentally in the vehicle when unattended. The vehicular processing device may then generate one or more a vehicle control signal(s) to automatically immobilize the vehicle (to prevent stealing) or engage systems such as ventilation, cooling or heating in order to protect the occupant until help arrives.

Automatic Feedback to the User Via a Virtual Help Agent

Unlike simple scripted or tree-based questions/answers approach, the processing device may be implemented with a fully personalized virtual agent application in order to process multimodal signals (including natural language processing—such as for speech recognition) using deep learning approaches for advice delivery.

One issue that arises, especially in relation to saving the user's data and any interaction of the system with the user, such as with a shared vehicle system, is the security of the saved data. This can be addressed if at least some of this data, such as the delivery of advice to the user (which can include medical advice) is enabled via blockchain in place of a classic database. The blockchain works on the basis of distributed network consensus with cystography, to make digital events (such as delivering advice, and the data to inform this advice) immutable and very hack resistant. For example, this can ensure integrity between disparate internet of things (IoT) sensors—particularly to enable interoperability with trust and shared accountability. It can allow a decentralized health exchange to reduce administration of the system required. The user can be assured of the privacy of the interaction—for example with a medical doctor.

In terms of the sharing of anonymous data for research purposes, blockchain can identify management features with pre-defined user access that can allow access to medical (and/or protected health information) and immutable storage of encrypted data.

It can be seen that several types of blockchain could deliver these benefits —including public, consensus, and private blockchain.

A public blockchain is by definition available to everybody, based on the tenets of cryptoeconomics, such as proof of work and proof of stake. Consensus and private blockchain mean that user access is restricted, but maintain some or much of the partial guarantees of authenticity that blockchains provide, with some or little decentralization. A consensus (basically a hybrid) blockchain could allow a group of health and wellness companies along with certain medical providers to collaborate to deliver a medical advice service, connecting IoT and other sensing devices, advice engines based on artificial intelligence (AI) and machine learning (ML), and smart contracts (payments on the same blockchain) between the user and physician to deliver targeted care.

Power Nap

The processing device 100 of the system can be programmed with a nap function to assist with a smart nap, whether the person is lying in bed or seat of a vehicle. For example, the user can tell the device "I am taking a nap." The interactive audio device can then audibly help the user fall asleep and then, by monitoring sleep and/or time, guide a person to an appropriate duration of nap based on the expected available time, an estimate of current sleep deficit, time of day, and user request. For example, it may optimize to target durations such as a 20 min, 30 min, 60 min or 90 min (full sleep cycle). The 60 min nap is to optimize deep sleep and allowing some time to recover at the end from any sleep inertia, whereas the 20 and 30 min target times are optimized to wake the user while they are still in light sleep, or before being in deep sleep for more than a minute or two. The time awake before sleep (nap) is also recorded in addition to the nap time.

A 20-25 min nap can be preferential to a 90 min full sleep cycle if the user is sleeping normally in the preceding days, as the longer period can impact sleep that night.

In an autonomous vehicle with or serving as processing device 100 of the system, the user could ask the device for a daytime nap (say at lunch). The vehicle can arrive to collect them, lull them to a nap by either driving quietly for the duration, or finding a safe place to park. This could be before or after the person has eaten, with a preference for the nap after lunch to allow time to digest (but may need to allow a little time such as 10-20 mins to reduce any possible acid reflux).

Example Vehicle Processing Applications

An example control processing methodology of the processing device 100 may be considered in reference to FIG. 8. At 802, the processing device may sense or detect presence in a vehicle cabin such as with the motion sensing methods previously described. At 804 a number of vehicle occupants may be determined. At 806, for the determined vehicle occupants, the processing device 806 may attempt to identify each occupant such as using biometric characteristics derived from motion sensing techniques as previously described. At 810, the processing device may access data or signals from other vehicular sensors (e.g., door closure status sensor, seat belt status sensors, wireless key/key fob detected etc.). Based on the sensors and/or motion sensing, at 812 the processing device determines that the vehicle is or had been locked state, such that no occupants were expected. At 814, the processing device detects, based on sensed physiological signals (e.g., respiration and/or cardiac signal in ranges attributable to children or infants), that only a child and/or infant occupies the vehicle. Alternatively, at 816, an occupant is detected but not recognized such that processing device may determine an unauthorized presence (intruder or stowaway). Based on the determinations at 816 or 814, the processing device generates output such as to trigger an alert (e.g., alarm or communication). At 820, the processing device may also generate output, based on the prior determinations, such as one or more control signals to a vehicle control system to disable the vehicle in the event of an intruder or stowaway. Optionally, at 820 in the event of a detected child/infant left behind, the generated output to a vehicle control system may be a control signal to activate a vehicle environmental control (e.g., ventilation and/or temperature control), for example.

At 822, the processing device determines, such as by key FOB detection and/or biometric identification, that the vehicle is in use/occupied by an authorized person. At 824, conducts a deep learning cardiorespiratory analysis, such as by the methods previously described. The processing device may then operate sleep analysis/detection processes at 824 as previously discussed, fatigue/alertness detection processes at 828 and/or medical screening/service processes at 830 such as using the motion sensing techniques described herein. At 832, the processing device may optionally generate output based on the detection processes at 826, 828 and 830 such as by engaging the user with audio/visual interactive communications (e.g., AI process and/or chatbot) using, for example, a speaker and microphone, coupled with the processing device. Additionally, at 834, the processing device may optionally generate output such as one or more control signals for setting or requesting operations of a vehicle control system (e.g., movement of the vehicle, adjustment of a light condition of the cabin vicinity, adjustment of electrochromic glass transparency, movement of a seat of the cabin vicinity, adjustment of a braking parameter, adjustment of an acceleration parameter, adjustment of a suspension setting, adjustment of window coverage, adjustment of an acoustic barrier, immobilization of the vehicle, engagement of vehicle ventilation and/or engagement of vehicle cabin cooling/heating system) based on the interactive communications and/or the processes at 826, 828 and 830. Additionally, at 834 and/or 832, output may be generated to communicate data including the nature of the detections made at 826, 828, 830 and 832. Optionally, at 836, data concerning the detected conditions may be recorded, such as in a secure manner. For example, the data may be stored by a blockchain process at 836.

FIG. 9 illustrates additional example processes that may be implemented by a vehicular processing device of the present technology, such as for audio based sensing. Optionally at 902, a vehicular processing device, such as an audio entertainment system in a housing (e.g., dashboard) of a vehicle, may receive a download of a processing application with control instructions for execution by one or more processors of the processing device. At 902, the processing device may check capabilities of the speaker/microphone of the system such as to confirm capability of generating and receiving low frequency ultrasonic sensing signals. At 904, setup processing may be run by the processing device to determine parameters for acoustic sensing. This may optionally involve generating and sensing various acoustic sensing signals. For example, at 906 audio probing sequences as previously described may be generated to map the internal area (cabin) of the vehicle. Optionally at 908, pre-configured values may be accessed based on known sensing characteristics (map) of the particular vehicle and sensing system.

Following these processes, the processing device may control generation and reception of sensing signals, such as by detecting one or more persons within the vehicle cabin at 910. Such sensing may be based on detection of motion and/or analysis of detected motion to detect physiological characteristics (e.g., cardiac motion and/or respiration motion). Such detection may serve to identify particular locations of the cabin that are occupied by a person. Upon confirmation of such detections, the processing device may activate one or more processes. For example, at 912, the processing device may detect ambient vehicle noise or other sounds in the environment (e.g., music voices, etc.) such as with a microphone. Such sounds may serve as information for filtering or adjusting of sensing signals as previously described. At 914, the processing device may determine, such as by access to vehicle control system sensors or vehicle sensors, climate control system settings. Such information may also serve as information for filtering or adjusting of sensing signals as previously described or assist in evaluation of physiological movement signals for their characterization. At 916, the processing device may access other vehicle sensor information such as determining steering wheel angle, accelerator/brake pedal setting, seat belt status, etc.). Such information may also serve as information for filtering or adjusting of sensing signals as previously described or assist in evaluation of physiological movement signals for their characterization. At 918, other sensors, such as chassis level, throttle, suspension, drive train, motor sensors, may be accessed. Such information may also serve as information for filtering or adjusting of sensing signals as previously described or assist in evaluation of physiological movement signals for their characterization. At 920, the processing device may perform physiological sensing (e.g., with acoustic sound generation SONAR) and characterization of motions that are detected with such sensing, such as according to any of the details previously described.

Figure 10:
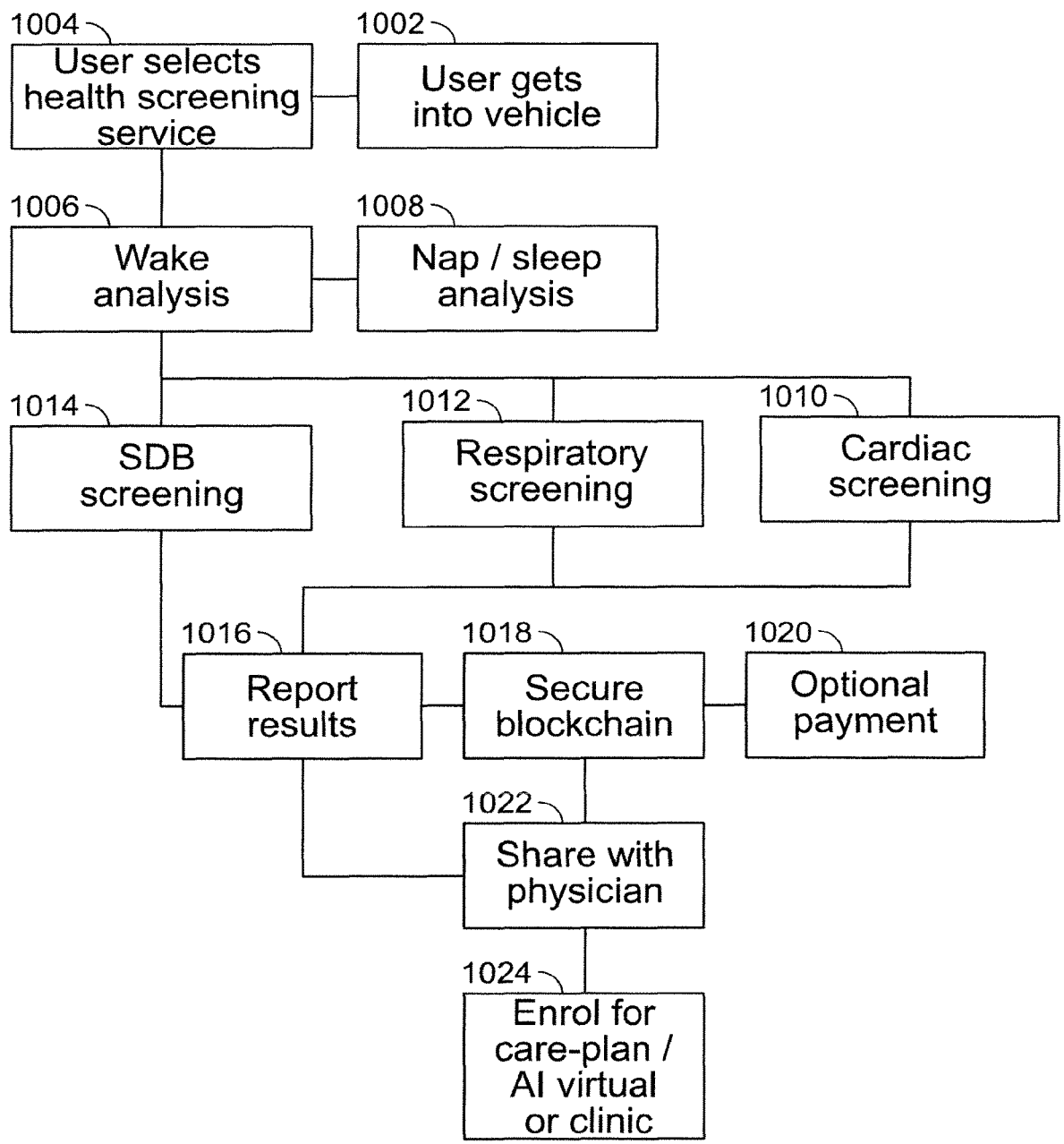
FIG. 10 illustrates example processing flow for a process for in-vehicle sensing of physiological parameters to implement an in-vehicle health assessment processing system and/or an in-vehicle sleep service system.

FIG. 10 illustrates additional example processes that may be implemented by a vehicular processing device of the present technology, such as for sensing in an semi-autonomous or autonomous vehicle. At 1002, the vehicular processing device detects entry of a user into the vehicle. At 1004, such as in response to an interactive query (e.g., natural language processing) by the processing device, the user is prompted to select a monitoring or screening service. At 1006, while the user is still awake, the processing device may begin sensing by the processes described herein to detect awake physiological characteristics. Such a process may optionally include a sleep inducement presentation such as with respiratory entrainment. At 1008, the processing device may perform sleep analysis (e.g., stage detections) and otherwise detect sleep. The processing device at 1008 may control a nap process (e.g., power nap) as previously described. At 1010, 1012 and 1014, the vehicular processing device may optionally perform health screening. For example, in an optional sleep disordered breathing detection process 1014, events of SDB may be detected via motion and/or sound sensing as previously described. Optionally, a respiratory screening detection process 1012, respiration may be monitored such as for detection of chronic disease conditions (e.g., worsening of heart failure) via motion and/or sound sensing as previously described. Optionally, in a cardiac screening detection process 1010, cardiac information may be monitored such as for detection of chronic disease conditions (e.g., worsening of heart failure) or other cardiac related occurrence via motion and/or sound sensing as previously described.

At 1016, the processing device may generate output based on the detections of any of the screening process(es). As described in more detail herein such output may be one or more vehicle related control signals and/or data indicating the detections of any of these processes. At 1018, data of the detections may be secured, such as with a blockchain recording process. At 1020, optional payment services may arrange for currency transfer, such as in relation to a charge for the screening, which may be based on the results and/or a transaction recorded in the blockchain data. At 1022, the processing device may communicate such result with a health care provider or emergency health service. Optionally, at 1024, the processing device may communication with a medical institution such as a clinic or hospital for services.

Figure 11:
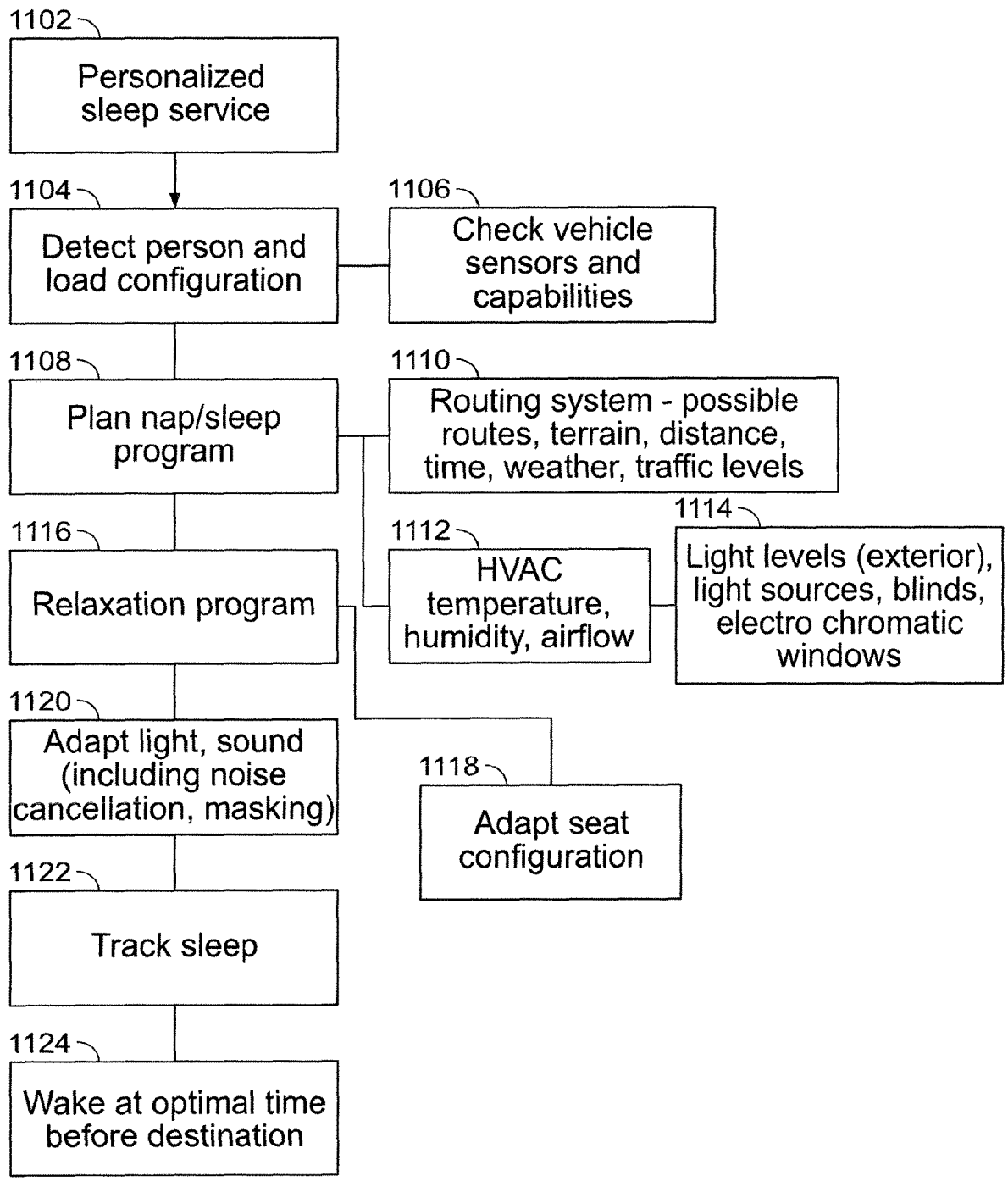
FIG. 11 illustrates example processing flow for a process with sensing of physiological parameters to implement an in-vehicle nap/sleep service system.

FIG. 11 illustrates example processes for a sleep or nap service, that may provide guided relaxing breathing exercises, and optionally use motors/servos/actuators in a seat to act as cues or tactile feedback. At 1102, a personalized sleep service is activated, such as with voice command recognition and/or presence detection by the vehicular processing device. At 1104, the processing device may detect load configuration and optionally perform biometric identification. At 1106, vehicle and sensor capabilities are determined, such as for meeting pre-existing a user parameters accessed based on the biometric identification. At 1108 a nap/sleep plan may be initiated such as to determine desired length of sleep time parameters. At 1110, a navigation system may compute a destination and route based on the sleep parameters as well as, for example, terrain information, distance information, sleep and travel time information, weather information and traffic information. Such a destination may optionally be provided by the user. Optionally, arrival at such a destination via the computed route may be controlled by an autonomous vehicle operations control system. At 1112 and 1114, cabin environment is controlled such as with a vehicle environment control system. As previously described, such control may include temperature, air, humidity, and light adjustments. At 1116, a sleep inducement or relaxation inducement presentation is made, such as with generated audio, tactile (e.g., seat adjustment) and visual output, for example by entraining breathing. At 1118, the processing device, via a vehicle operations control system may adjust a seat characteristic to move the seat to a comfortable position and formation for the user. At 1120, the processing device may further adapt light and sound in the vehicle, such as with noise cancellation and noise masking generation (e.g., white noise). At 1122, the user's sleep is tracked by the processing device, such as by sensing motion as described herein to determine sleep, sleep time, sleep score, sleep stage, etc.) At 1124, the processing device, such as at a predetermined time, sleep stage, and destination, may generated output to wake the user, such as with controlling generation of sound, seat motion and/or light adjustments in the vehicle.

5.2 Other Remarks

A portion of the disclosure of this patent document contains material which is subject to copyright protection. The copyright owner has no objection to the facsimile reproduction by anyone of the patent document or the patent disclosure, as it appears in Patent Office patent files or records, but otherwise reserves all copyright rights whatsoever.

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the present technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated herein by reference in their entirety to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

The terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular examples, it is to be understood that these examples are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilized to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative examples and that other arrangements may be devised without departing from the spirit and scope of the technology.

The invention claimed is:

1. A non-transitory processor-readable medium, having stored thereon processor-executable instructions which, when executed by a processor of an electronic device, cause the processor to process data sensed in a cabin vicinity of a vehicle, to detect physiological movement of a user, the processor-executable instructions comprising:
   instructions to control producing a sensing signal in the cabin vicinity of a vehicle;
   instructions to control sensing, with a sensor, a reflected signal from the cabin vicinity of the vehicle;
   instructions to derive a physiological movement signal with at least a portion of the sensed reflected signal and a signal representative of at least a portion of the sensing signal;
   instructions to operate the electronic device to provide a sleep service, wherein, based on an evaluation of at least a portion of the derived physiological movement signal, the sleep service generates an output, wherein the sleep service is configured to operate one or both of (a) a relaxation program presentation, and (b) an initiation of a sleep plan, wherein the sleep service accesses pre-existing user parameters for operating the sleep service based on identifying the user by biometric identification performed by the electronic device;
   wherein the relaxation program presentation comprises guided breathing exercises; and
   wherein the guided breathing exercises comprise cues or tactile feedback generated by actuators in a seat of the vehicle.

2. The processor-readable medium of claim 1, wherein the sleep plan comprises a desired length of sleep time parameter.

3. The processor-readable medium of claim 2, further comprising instructions to control a navigation system of the vehicle based on the desired length of sleep time parameter.

4. The processor-readable medium of claim 3, wherein the navigation system computes a destination and route based on the desired length of sleep time parameter.

5. The processor-readable medium of claim 4, wherein the navigation system computes the destination and route (a) based on one or more of terrain information, weather information and traffic information; and (b) based on one or more of distance information and travel time.

6. The processor-readable medium of claim 1, wherein the relaxation program presentation comprises generated audio, tactile and/or visual output.

7. The processor-readable medium of claim 1, wherein the relaxation program presentation operates a vehicle operations control system comprising a motor to adjust a seat characteristic to change seat formation for the user.

8. The processor-readable medium of claim 1, wherein the sleep service controls the electronic device to adapt light in the vehicle.

9. The processor-readable medium of claim 8, wherein the sleep service is configured to adapt light by operation of any of a blind or electro-chromatic window.

10. The processor-readable medium of claim 1, wherein the sleep service controls adapting sound in the vehicle to cancel or mask noise.

11. The processor-readable medium of claim 1, wherein the sleep service further comprises tracking a user's sleep by determining one or more of sleep time, sleep score, and sleep stage.

12. The processor-readable medium of claim 11, wherein the sleep service is configured to generate output to wake the user at one or more of a predetermined time, sleep stage and destination.

13. The processor-readable medium of claim 11, wherein the sleep service generates the output to wake the user by controlling seat motion and light in the vehicle.

14. The processor-readable medium of claim 1, wherein the sensing signal is any one or more of a radio frequency sensing signal generated by a radio frequency transmitter coupled with the electronic device, an acoustic sensing signal generated by a speaker coupled with the electronic device, and an infrared sensing signal generated by an infrared emitter coupled with the electronic device.

15. The processor-readable medium of claim 1, wherein the derived physiological movement signal comprises one or more of a respiratory motion, gross motion, or a cardiac motion, of a user within the cabin vicinity.

16. The processor-readable medium of claim 1, wherein the evaluation of the derived physiological movement signal comprises determining any one or more of breathing rate, amplitude of breathing, relative amplitude of breathing, cardiac rate, cardiac amplitude and relative cardiac amplitude.

17. Apparatus including an electronic device that comprises: one or more processors coupled to one or more sensors operating in a cabin vicinity of a vehicle; and configured to execute the processor-executable instructions of the processor-readable medium of claim 1.

18. A method of one or more processors of an electronic device to detect physiological movement of a user in a cabin vicinity of a vehicle, the method comprising:
  controlling producing a sensing signal in the cabin vicinity of a vehicle;
  controlling sensing, with a sensor, a reflected signal from the cabin vicinity of the vehicle;
  deriving a physiological movement signal with at least a portion of the sensed reflected signal and a signal representative of at least a portion of the sensing signal;
  operating the electronic device to provide a sleep service, wherein, based on an evaluation of at least a portion of the derived physiological movement signal, the sleep service generates an output, wherein the sleep service is configured to operate one or both of (a) a relaxation program presentation, and (b) an initiation of a sleep plan, wherein the sleep service accesses pre-existing user parameters for operating the sleep service based on identifying the user by biometric identification performed by the electronic device;
  wherein the relaxation program presentation comprises guided breathing exercises; and
  wherein the guided breathing exercises comprise cues or tactile feedback generated by actuators in a seat of the vehicle.

19. The processor-readable medium of claim 1, wherein the sleep service is activated by voice command recognition and/or presence detection performed by the electronic device.

20. The processor-readable medium of claim 1, wherein the sleep service is configured to check vehicle sensors and capabilities based on a configuration of the pre-existing user parameters.

\* \* \* \* \*